(12) United States Patent
Geibel et al.

(10) Patent No.: US 8,093,299 B2
(45) Date of Patent: Jan. 10, 2012

(54) METHODS OF TREATING BOWEL DISORDERS

(75) Inventors: John Peter Geibel, Branford, CT (US);
Steven Charles Hebert, Woodbridge, CT (US); Patricia Hebert, legal representative, Woodbridge, CT (US); David Martin, Camarillo, CA (US); Deborah A. Russell, Newbury Park, CA (US)

(73) Assignees: Amgen Inc., Thousand Oaks, CA (US); Yale University, New Haven, CT (US)

( * ) Notice: Subject to any disclaimer, the term of this patent is extended or adjusted under 35 U.S.C. 154(b) by 345 days.

(21) Appl. No.: 12/080,086

(22) Filed: Mar. 31, 2008

(65) Prior Publication Data

US 2009/0018135 A1  Jan. 15, 2009

Related U.S. Application Data

(60) Provisional application No. 60/921,132, filed on Mar. 30, 2007.

(51) Int. Cl.
*A61K 31/138* (2006.01)

(52) U.S. Cl. ........................................... 514/650

(58) Field of Classification Search ................ None
See application file for complete search history.

(56) References Cited

U.S. PATENT DOCUMENTS

| | | | |
|---|---|---|---|
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,214,373 B1 | 4/2001 | Snowden et al. | |
| 6,395,273 B1 | 5/2002 | Kink et al. | |
| 6,395,919 B1 | 5/2002 | Bhatnagar et al. | |
| 6,613,751 B2 | 9/2003 | Raz et al. | |
| 6,858,595 B2 | 2/2005 | Hayes et al. | |
| 6,861,053 B1 | 3/2005 | Lin et al. | |
| 2004/0063784 A1 | 4/2004 | Kelly et al. | |
| 2004/0219232 A1 | 11/2004 | Lipton et al. | |
| 2004/0242602 A1 | 12/2004 | Gungor et al. | |

FOREIGN PATENT DOCUMENTS

| | | |
|---|---|---|
| WO | WO 02/49651 | 6/2002 |
| WO | WO 2004/089415 | 10/2004 |
| WO | WO 2004/091622 | 10/2004 |
| WO | WO 2004/106295 | 12/2004 |
| WO | WO 2007/027548 | 3/2007 |
| WO | WO 2007/112280 | 10/2007 |
| WO | WO 2007/124465 | 11/2007 |
| WO | WO 2008/057282 | 5/2008 |

OTHER PUBLICATIONS

The Merck Manual, 17th edition (1999), pp. 302-307.*
Nemeth et al., TEM, 10(2), (1999), pp. 66-71.*
Almy et al., "Chronic and recurrent diarrhea", Disease-A-Month, 1 (10), 2-32 (1955).
Persson et al., "Gastrin releases a blood calcium-loweing peptide from the acid-producing part of the rat stomach", Prac. Natl. Acad. Sci., 86:2834-2388 (1989).
Agreus et al., "Irritable bowel syndrome and dyspepsia in the general population: overlap and lack of stability of time", Gastroenterology, 109:671-680 (1995).
Igarashi et al., "Effect of calcimimetic agen, KRN568, on gastrin secretion in healthy subjects", Endrocrine Journal, 47 (5) 517-523, 2000.
Pimentel et al., "Normalization of lactulose breath testing correlates with symptom improvement in irritable bowel syndrome improvement in irritable bowel syndrome. A doulble-blind, randomized, placebo-controlled study", The American Journal of Gastroenterology, 98 (2), 412-419, 2003.
Hebert et al., "Functions and roles of the extracellular $Ca^{2-}$—sensing receptor in the gastrointestinal tract", Cell Calcium, 35:239-247 (2004).
Loftus, Jr. et al., "Clinical epidemiology of inflammatory bowel diseases: Incidence, prevalence, and environmental influences", Gastroenterology, 126:1504-1517, (2004).
Lakatos et al., "Recent trends in the epidemiology of inflammatory bowel diseases: Up or down?", World Journal of Gastroenterology, 12 (38), 6102-6108 (2006).
Resta-Lenert et al., "Antibiotics versus probiotic treatments in the mdr1a 1/1 mouse model of colitis", Gastrointestinal Pathophysiology, 772.1, XP009103790.

* cited by examiner

*Primary Examiner* — Phyllis G. Spivack
(74) *Attorney, Agent, or Firm* — Olga Mekhovich

(57) ABSTRACT

The present invention relates to methods for treating bowel disorders using calcimimetics.

3 Claims, 11 Drawing Sheets

Distal Colon

Colon All Segments

Proximal Colon
(D-152-I2)

Proximal Colon

\# $P<0.01$ vs. Control
\* $P<0.001$ vs. TTX

Distal Colon
(D-151-I1)

Distal Colon

\# P<0.001 vs. Control
\* P<0.001 vs. TTX

Proximal Colon
(D-153-I2)

Proximal Colon

\# P<0.01 vs. Control
\* P<0.001 vs. comp A

Distal Colon
(D-153-I1)

Distal Colon

\# P<0.001 vs. Control
\* P<0.001 vs. comp A

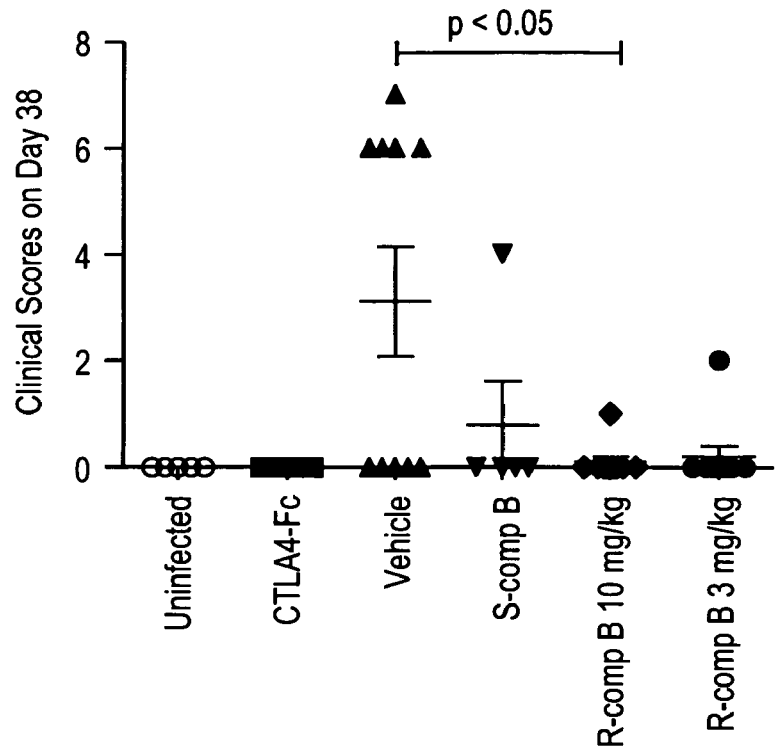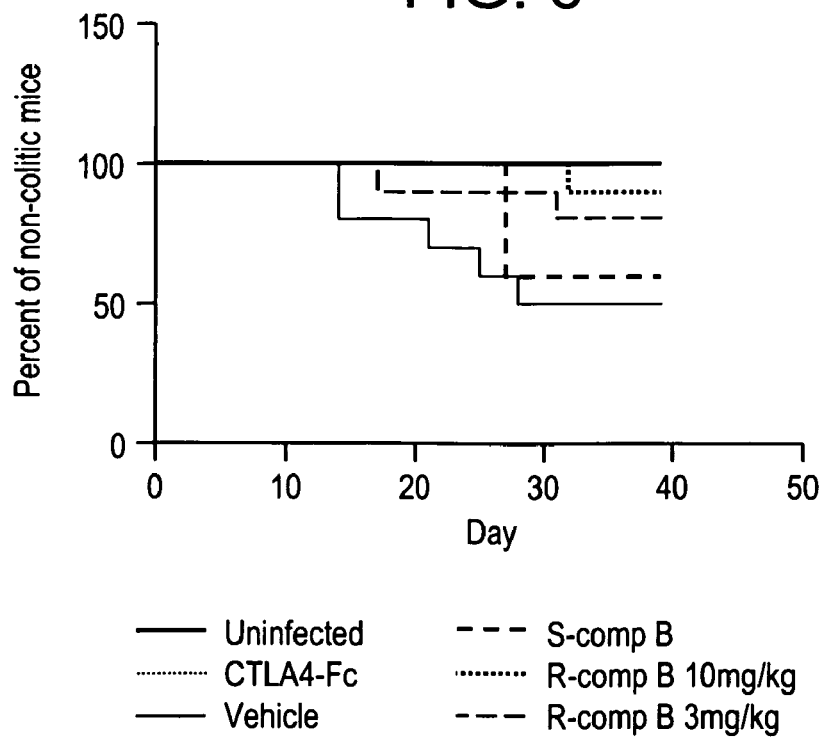

METHODS OF TREATING BOWEL DISORDERS

FIELD OF THE INVENTION

This invention relates generally to the field of medicine and, more specifically, to methods for treating or preventing bowel disorders, in particular, inflammatory bowel disease and irritable bowel syndrome.

BACKGROUND OF THE INVENTION

Approximately 3.6 million people in the US and Europe (Lotus, E. (2004) *Gastroenterol.* 126: 1504-1517) and about 15.8 million people worldwide have inflammatory bowel disease or IBD (Lakatos, P. (2006) *World J. Gastroenterol.* 12(38): 6102-6108). IBD is a collective term used to describe two gastrointestinal disorders of unknown etiology; Chron's disease (CD) and ulcerative colitis (UC). Both diseases appear to result from the unrestrained activation of an inflammatory response in the intestine. Ulcerative colitis occurs in the large intestine, while Chron's disease can involve the entire gastrointestinal tract, as well as the small and large intestines. It has been suggested that the pathogenesis of IBD is multifactorial involving susceptibility genes and environmental factors Sartor et al. (1997) *Am. J. Gastroenterol.* 92: 5S-11S. Although the causative triggers remain unclear, the role of a persistent and likely dysregulated mucosal immune response is central to the pathogenesis of IBD. It remains unclear whether the persistent inflammation, an intrinsic feature of IBD, reflects a primary aberration in mucosal response or results from an inappropriate persistent stimulation. *Curr. Opin. Gastroenterol.* (2003) 19(4): 336-342. The course and prognosis of IBD varies widely. For most patients, it is a chronic condition with symptoms lasting for months to years. IBD is most common in young adults, but can occur at any age. The clinical symptoms of IBD include intermittent rectal bleeding, fever, abdominal pain, and diarrhea, which may range from mild to severe. Additional common signs of IBD are anemia and weight loss. 10 to 15% of all IBD patients will require surgery over ten year period. Protracted IBD is a risk factor for colon cancer, and the risk begins to rise significantly after eight to ten years of IBD.

The first line therapy that is often used for IBD is aminosalicylates, which include sulfasalazine and the brands Asacol, Pentasa, Dipentum, and Colazal. Treatment for Chron's disease takes a stepwise approach with nutritional supplements and 5-ASA often used as chronic therapy aimed at prophylaxis against flare-up of the disease. Some physicians believe that 5-ASAs are not effective in CD and start with a steroid such as budesonide. When mild to moderate patients flare up, they are often treated with a short course of steroids. For more severe patients or those with more frequent flares, immunosuppressices such as azathioprine (Imuran), 6-MP, and methotrexate are used. The anti-TNF antibody Remicade is also used to treat Chron's disease. Treatment of ulcerative colitis is very similar to treatment of Chron's disease, following a similar stepwise approach with the use of 5-ASAs, short courses of steroids, other immunosuppressives and surgery. Remicade is sometimes used for severe disease not responding to steroids or traditional immune modulators. Methotrexate and antibiotics are generally not used in UC and it's believed by many physicians that methotrexate does not work in UC. Need for surgery is more prevalent in UC than in CD, with 25-40% of patients eventually requiring colectomy. Unlike in Chron's disease, surgery for ulcerative colitis is curable. There are unmet needs for IBD patients who fail on all of the currently available therapies. Approximately 20% of patients fail all therapies and need surgery in the short term, 40% of patients will require surgery in the long term.

Irritable bowel syndrome, or IBS, is the most prevalent digestive disease, accounting for 12% of visits to primary care physicians and 28% of referrals to gastroenterologists. IBS is one of a heterogeneous family of functional gastrointestinal disorders, which are difficult to treat because no single etiology for these disorders is known and thus treatment is directed at controlling symptoms. IBS affects at least 10 to 20% of adults in the US, mostly women, and second only to the common cold as a cause of absenteeism from work. The majority of cases are undiagnosed because only 25-30% of patients seek medical attention (International Foundation for Functional Gastrointestinal Disorders). IBS produces disability rates equal to or greater than severe organic gastrointestinal disease. One study reported that 8% of patients with IBS retire early due to their symptoms. Rees, G. et al. (1994) *J. R. Soc. Health* 114: 182. IBS is characterized by altered bowel habits and abdominal pain, typically in the absence of detectable structural abnormalities. No clear diagnostic markers exist for IBS, and its definition is based on its clinical presentation. IBS is often confused with IBD, colitis, mucous colitis, spastic colon, or spastic bowel. Only recently physicians started considering IBS to be a brain-gut functional disorder, rather than a somatic manifestation of physiological stress. The Rome diagnostic criteria of IBS (currently, Rome II) can be used to rule out other disorders. According to the Rome II criteria, abdominal pain or discomfort is a prerequisite clinical feature of IBS. Drossman D. et al. (eds) Rome II: the functional gastrointestinal disorders: diagnosis, pathophysiology, and treatment: a multinational consensus. McLean, V A: Degnon Associates, 2000. Most IBS patients experience several IBS symptoms such as abdominal pain, altered bowel habits, flatulence, upper GI symptoms such as dyspepsia, heartburn nausea, and vomiting. IBS patients typically fall into two broad clinical groups. Most patients belong to the first group, presenting with abdominal pain associated with altered bowel habit that include constipation diarrhea or alternating constipation and diarrhea. The second group of patients have painless diarrhea. It is generally believed that the central nervous system plays an important role in the pathogenesis of IBS. This is supported by the clinical association of emotional disorders and stress with IBS symptom exacerbation, and the therapeutic response to IBS therapies that act on cerebral cortical sites.

About 80% of IBS patients are treated with some form of therapy. The management approach for IBS depends on the patient's predominant symptoms. The goal in patients with constipation-predominant IBS (IBS-C) is to stimulate a bowel movement, thus, bulk fiber laxatives can be used several times per day. Second line therapy may involve Senekot and antispasmodics (e.g., Levsin) for periodic cramping and abdominal pain. Third line therapy may include Zelnorm. Usually, 40% of patients with IBS-C improve with treatment. In patients with diarrhea-predominant IBS, lactose intolerance and bacterial overgrowth must be ruled out first. Imodium is standard treatment for this type of IBS. Lotronex is rarely used and reserved only for the very severe patients due to risk of ischemic colitis. 60% of diarrhea-predominant IBS (IBS-D) patients improve with treatment. Patients with mixed-symptom IBS (IBS-A) may be treated with a combination of approaches depending on whether the patient is experiencing a period of constipation or diarrhea. A portion of these patients are also likely to be IBS-D or IBS-C patients that get overmedicated and swing to the other extreme. Most long-term studies of IBS report that symptoms persist for more than five years in greater than 75% of patients despite appropriate therapy.

Bowel disorders such as IBD and IBS are a medical problem, and improved methods of treatment are necessary as no satisfactory treatments are currently available.

SUMMARY OF THE INVENTION

The present invention provides methods for treating or preventing bowel disorders comprising administering to a subject in need thereof a therapeutically acceptable dose of a pharmaceutical composition comprising a calcimimetic compound and a pharmaceutically acceptable diluents or carrier.

In one aspect, the bowel disorder can be inflammatory bowel disease (IBD). In one aspect, the IBD can be ulcerative colitis (UC). In another aspect, the IBD can be Chron's disease (CD). IBD can be mild, moderate, or severe. The methods of the invention can further comprise nutritional management. In one aspect, the nutritional management can comprise administration of calcium, magnesium, zinc, iron, folate, vitamin $B_{12}$, vitamin D, or vitamin K. In one aspect, the methods of the invention can further comprise administering an antidiarrheal agent. The antidiarrheal agent can be loperamide or diphenoxylate. In another aspect, the methods of the invention can further comprise administering an antispasmodic agent. In a further aspect, methods of the invention can further comprise administering an anticholinergic agent or an analgesic agent. In another aspect, the methods of the invention can further comprise administering a 5-aminosalicylic compound. In a further aspect, the methods of the invention can further comprise administering an immunomodulator. In another aspect, the methods of the invention can further comprise administering an antibiotic. In one aspect, methods of the invention can be practiced in conjunction with a surgical treatment.

In one aspect, the bowel disorder can be irritable bowel syndrome (IBS). In one aspect, the IBS can be a constipation predominant IBS. In another aspect, the IBS can be a diarrhea predominant IBS or a mixed symptom IBS. In one aspect, the methods of the invention can further comprise nutritional management. In one aspect, the nutritional management can comprise limiting fat intake, restricting intake of poorly digestible sugars, limiting of foods associated with increased flatulence, increased fiber intake, or addition of probiotics. In another aspect, the methods of the invention can further comprise administering a laxative. In a further aspect, the methods of the invention can further comprise administering an opiate-based agent, an anti-spasmodic agent, an anti-depressant agent or a prokinetic agent. In another aspect, the methods of the invention can further comprise administering a peripheral dopamine receptor agonist, a hormonal treatment or a tranquilizer. In a further aspect, the methods of the invention can further comprise psychological therapy, cognitive therapy, biofeedback and stress reduction technique, or hypnosis.

In a further aspect, the bowel disorder can be lymphocytic colitis, collagenous colitis, diversion colitis, endometriosis, caustic enema-induced colitis, drug-induced ischemic colitis, NSAID-induced ulcer, nonspecific ulcer, stercoral ulcer, solitary rectal ulcer, typhilitis, colitis cystica profunda, pneumatosis cystoides intestinalis, or malakoplakia.

The calcimimetic compounds useful in the methods of the present invention are described in detail in Detailed Description below.

In one aspect, the subject can be mammal. In one aspect, the subject can be human.

BRIEF DESCRIPTION OF THE DRAWINGS

FIG. 5 represents clinical score on the final day of study (day 38) for controls and compound B. scores are calculated by summing the stool score (0-4) and the anal inflammation score (0-4) and averaging the scores for the group (maximal score is 8). Error bars represent SEM.

FIG. 6 represents disease onset graph. Curve representing the percentage of mice showing signs of colitis at various time points throughout the study. Day of disease onset is determined by a subject having two consecutive days of positive clinical score. The 10 mg/kg Compound B group was significantly different from the vehicle control group.

DETAILED DESCRIPTION OF THE INVENTION

I. Definitions

Figure 1A:
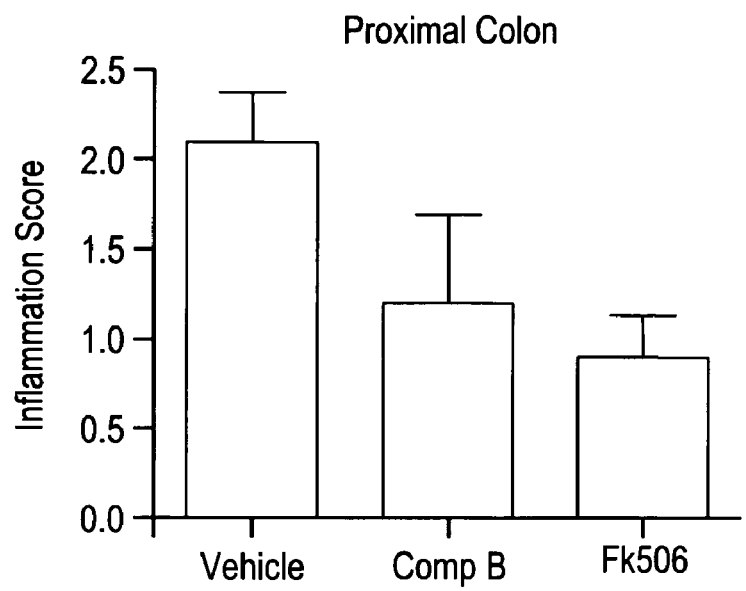
FIG. 1 illustrates the effect of the calcimimetic compound B on colonic inflammation in 5% DSS induced colitis model. Panel A, proximal colon; Panel B, middle colon, Panel C, distal colon; Panel D, combined colon.
Figure 1B:
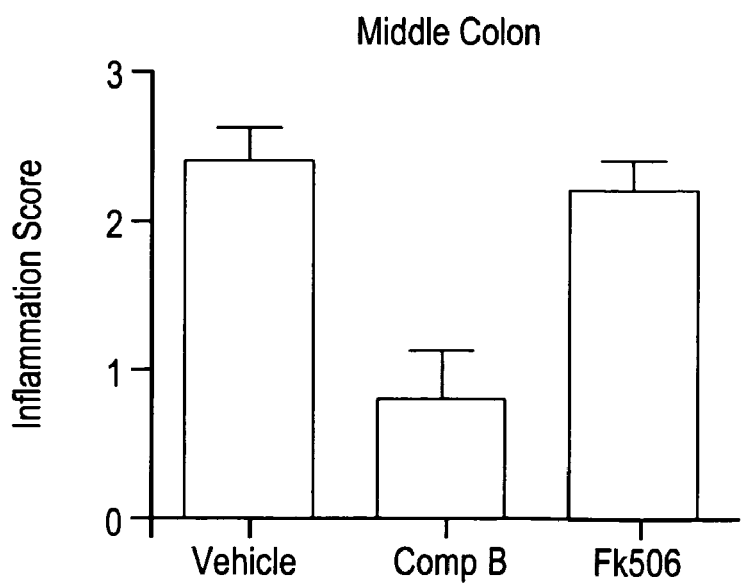
Figure 1C:
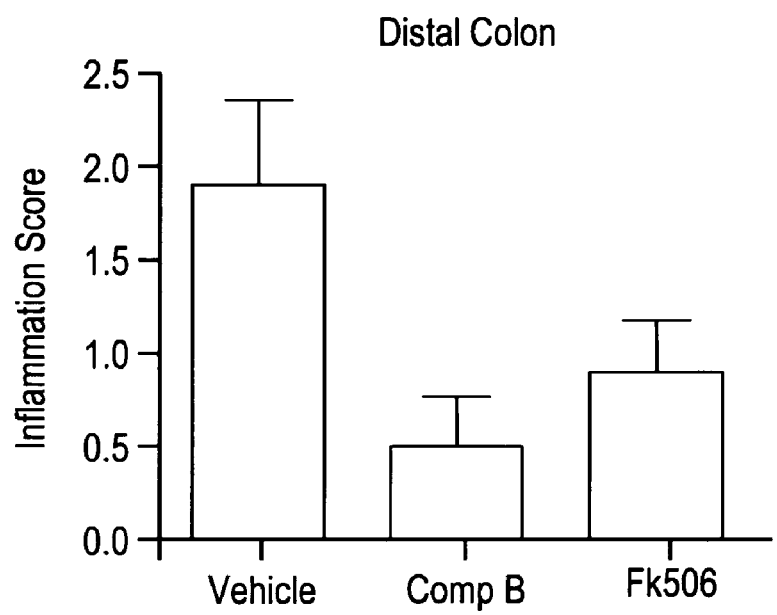
Figure 1D:
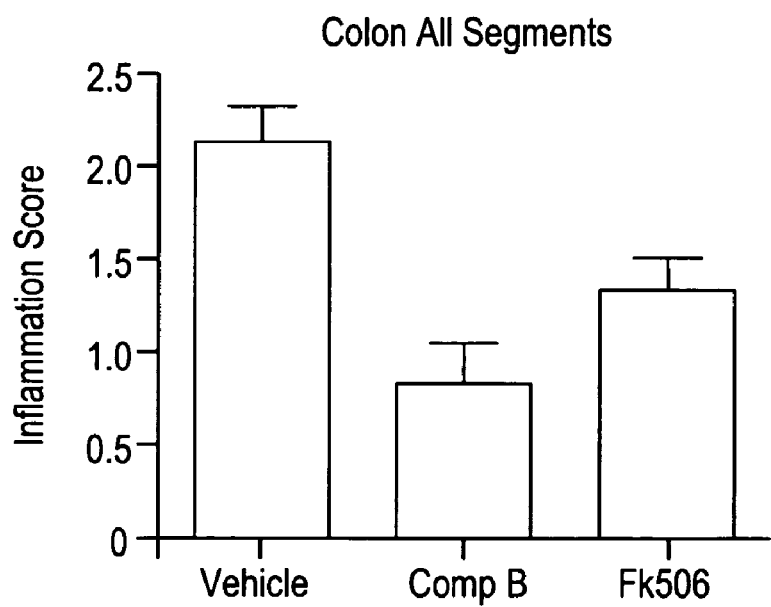

As used herein, the term "subject" is intended to mean a human, or an animal, in need of a treatment. This subject can have, or be at risk of developing, a bowel disorder, for example, inflammatory bowel disorder or irritable bowel syndrome.

"Treating" or "treatment" of a disease includes: (1) inhibiting the disease, e.g., arresting or reducing the development of the disease or any of its clinical symptoms, or (2) relieving the disease, e.g., causing regression of the disease or any of its clinical symptoms.

Administration "in combination with" or "together with" one or more further therapeutic agents includes simultaneous or concurrent administration and consecutive administration in any order.

The phrase "therapeutically effective amount" is the amount of the compound of the invention that will achieve the goal of improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

The phrase "bowel disorders" includes but is not limited to IBD, IBS, diverticular disease, collagenous and lymphatic colitis, diversion colitis, endometriosis, typhlitis, colitis, cystica profunda, pneumatosis cystoides intestinalis, and malakoplakia.

II. Calcimimetic Compounds and Pharmaceutical Compositions Comprising Them, Administration and Dosage A. Calcimimetic Compounds, Definitions As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less that 30 seconds (for example, by mobilizing internal calcium); it evokes a rapid increase in $[Ca^{2+}{}_i]$, occurring within thirty seconds; it evokes a sustained increase (greater than thirty seconds) in $[Ca^{2+}{}_i]$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}{}_i]$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V. In one aspect, a calcimimetic compound can be a small molecule. In another aspect, a calcimimetic can be an agonistic antibody to the CaSR.

Calcimimetic compounds useful in the present invention include those disclosed in, for example, European Patent Nos. 637,237, 657,029, 724,561, 787,122, 907,631, 933,354, 1,203,761, 1,235 797, 1,258,471, 1,275,635, 1,281,702, 1,284,963, 1,296,142, 1,308,436, 1,509,497, 1,509,518, 1,553,078; International Publication Nos. WO 93/04373, WO 94/18959, WO 95/11221, WO 96/12697, WO 97/41090, WO 01/34562, WO 01/90069, WO 02/14259, WO 02/059102, WO 03/099776, WO 03/099814, WO 04/017908; WO 04/094362, WO 04/106280, WO 06/117211; WO 06/123725; WO 07/060,026; WO 08/006,625; WO 08/019,690; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,750,255, 6,908,935, 7,157,498, 7,176,322 and U.S. Patent Application Publication Nos. 2002/0107406, 2003/0008876, 2003/0144526, 2003/0176485, 2003/0199497, 2004/0006130, 2004/0077619, 2005/0032796, 2005/0107448, 2005/0143426, European patent application PCT/EP2006/004166, French patent application 0511940.

In certain embodiments, the calcimimetic compound is chosen from compounds of Formula I and pharmaceutically acceptable salts thereof:

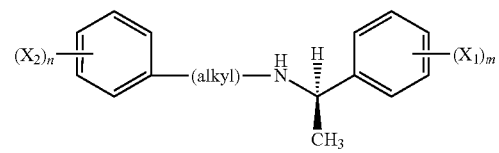

wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene dioxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from C1-C3 alkyl radicals, which are optionally substituted with at least one group chosen from saturated and unsaturated, linear, branched, and cyclic C1-C9 alkyl groups, dihydroindolyl and thiodihydroindolyl groups, and 2-, 3-, and 4-piperid(in)yl groups.

The calcimimetic compound may also be chosen from compounds of Formula II:

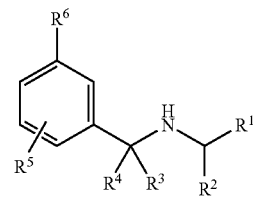

and pharmaceutically acceptable salts thereof, wherein:

$R^1$ is aryl, substituted aryl, heterocyclyl, substituted heterocyclyl, cycloalkyl, or substituted cycloalkyl;

$R^2$ is alkyl or haloalkyl;

$R^3$ is H, alkyl, or haloalkyl;

$R^4$ is H, alkyl, or haloalkyl;

each $R^5$ present is independently selected from the group consisting of alkyl, substituted alkyl, alkoxy, substituted alkoxy, halogen, —C(=O)OH, —CN, —$NR^dS(=O)_mR^d$, —$NR^dC(=O)NR^dR^d$, —$NR^dS(=O)_mNR^dR^d$, or —$NR^dC(=O)R^d$;

$R^6$ is aryl, substituted aryl, heterocyclyl, substituted heterocyclyl, cycloalkyl, or substituted cycloalkyl;

each $R^a$ is, independently, H, alkyl or haloalkyl;

each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl, each of which may be substituted or unsubstituted;

each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, —C(=O)$R^c$, —O$R^b$, —N$R^aR^a$, —N$R^aR^b$, —C(=O)O$R^c$, —C(=O)N$R^aR^a$, —OC(=O)$R^c$, —N$R^a$C(=O)$R^c$, —N$R^a$S(=O)$_nR^c$ and —S(=O)$_n$N$R^aR^a$;

m is 1 or 2;
n is 0, 1 or 2; and
p is 0, 1, 2, 3, or 4;

provided that if $R^2$ is methyl, p is 0, and $R^6$ is unsubstituted phenyl, then $R^1$ is not 2,4-dihalophenyl, 2,4-dimethylphenyl, 2,4-diethylphenyl, 2,4,6-trihalophenyl, or 2,3,4-trihalophenyl. These compounds are described in detail in published US patent application number 20040082625.

In one aspect, the calcimimetic compound can be N-((6-(methyloxy)-4'-(trifluoromethyl)-1,1'-biphenyl-3-yl)methyl)-1-phenylethanamine, or a pharmaceutically acceptable salt thereof. In another aspect, the calcimimetic compound can be (1R)-N-((6-chloro-3'-fluoro-3-biphenylyl)methyl)-1-(3-chlorophenyl)ethanamine, or a pharmaceutically acceptable salt thereof. In a further aspect, the calcimimetic compound can be (1R)-1-(6-(methyl oxy)-4'-(trifluoromethyl)-3-biphenylyl)-N-((1R)-1-phenylethyl)ethanamine, or a pharmaceutically acceptable salt thereof.

In certain embodiments of the invention the calcimimetic compound can be chosen from compounds of Formula III

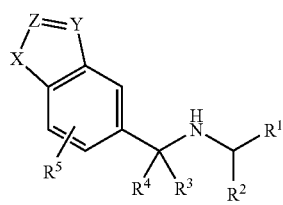

III and pharmaceutically acceptable salts thereof, wherein:

═════ represents a double or single bond;
$R^1$ is $R^b$;
$R^2$ is $C_{1-8}$ alkyl or $C_{1-4}$ haloalkyl;
$R^3$ is H, $C_{1-4}$ haloalkyl or $C_{1-8}$ alkyl;
$R^4$ is H, $C_{1-4}$ haloalkyl or $C_{1-4}$ alkyl;
$R^5$ is, independently, in each instance, H, $C_{1-8}$alkyl, $C_{1-4}$haloalkyl, halogen, —O$C_{1-6}$alkyl, —N$R^aR^d$ or N$R^d$C(=O)$R^d$;
X is —C$R^d$=N—, —N=C$R^d$—, O, S or —N$R^d$—;
when ═════ is a double bond then Y is =C$R^6$— or =N— and Z is —C$R^7$= or —N=; and when ═════ is a single bond then Y is —C$R^aR^6$— or —N$R^d$— and Z is —C$R^aR^7$— or —N$R^d$—; and
$R^6$ is $R^d$, $C_{1-4}$haloalkyl, —C(=O)$R^c$, —O$C_{1-6}$alkyl, —O$R^b$, —N$R^aR^a$, —N$R^aR^b$, —C(=O)O$R^c$, —C(=O)N$R^aR^a$, —OC(=O)$R^c$, —N$R^a$C(=O)$R^c$, cyano, nitro, —N$R^a$S(=O)$_mR^c$ or —S(=O)$_m$N$R^aR^a$;
$R^7$ is $R^d$, $C_{1-4}$haloalkyl, —C(=O)$R^c$, —O$C_{1-6}$alkyl, —O$R^b$, —N$R^aR^a$, —N$R^aR^b$, —C(=O)O$R^c$, —C(=O)N$R^aR^a$, —OC(=O)$R^c$, —N$R^a$C(=O)$R^c$, cyano, nitro, —N$R^a$S(=O)$_mR^c$ or —S(=O)$_m$N$R^aR^a$; or $R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from $C_{1-4}$alkyl;

$R^a$ is, independently, at each instance, H, $C_{1-4}$haloalkyl or $C_{1-6}$alkyl;
$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —O$C_{1-6}$alkyl, cyano and nitro;
$R^c$ is, independently, at each instance, $C_{1-6}$alkyl, $C_{1-4}$haloalkyl, phenyl or benzyl;
$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$ alkyl, phenyl, benzyl, naphthyl and heterocycle are substituted by 0, 1, 2, 3 or 4 substituents selected from $C_{1-6}$alkyl, halogen, $C_{1-4}$haloalkyl, —O$C_{1-6}$alkyl, cyano and nitro, $R^b$, —C(=O)$R^c$, —O$R^b$, —N$R^aR^b$, —N$R^aR^b$, —C(=O)O$R^c$, —C(=O)N$R^aR^a$, —OC(=O)$R^c$, —N$R^a$C(=O)$R^c$, —N$R^a$S(=O)$_mR^c$ and —S(=O)$_m$N$R^aR^a$; and m is 1 or 2.

Compounds of Formula III are described in detail in U.S. patent application 20040077619.

In one aspect, a calcimimetic compound is N-(3-[2-chlorophenyl]-propyl)-R-■-methyl-3-methoxybenzylamine HCl (Compound A). In another aspect, a calcimimetic compound is N-((6-(methyloxy)-4'-(trifluoromethyl)-1,1'-biphenyl-3-yl)methyl)-1-phenylethanamine (Compound B).

In one aspect, the calcimimetic compound of the invention can be chose from compounds of Formula IV

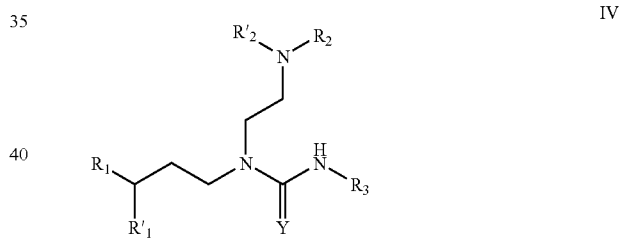

IV wherein:

Y is oxygen or sulphur;
$R_1$ and $R'_1$ are the same or different, and each represents an aryl group, a heteroaryl group, or $R_1$ and $R'_1$, together with the carbon atom to which they are linked, form a fused ring structure of formula:

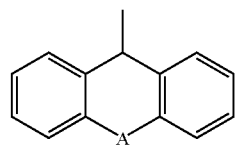

in which A represents a single bond, a methylene group, a dimethylene group, oxygen, nitrogen or sulphur, said sulphur optionally being in the sulphoxide or sulphone forms, wherein each of $R_1$ and $R'_1$, or said fused ring structure formed thereby, is optionally substituted by at least one substituent selected from the group c, wherein the group c consists of: halogen atoms, hydroxyl, carboxyl, linear and branched alkyl, hydroxyalkyl, haloalkyl, alkylthio, alkenyl, and alkynyl groups; linear and branched alkoxyl groups; linear and branched thioalkyl groups; hydroxycarbonylalkyl; alkylcarbonyl; alkoxycarbonylalkyl; alkoxycarbonyl; trifluoromethyl; trifluoromethoxy; —CN; —NO$_2$; alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different, R$_2$ and R'$_2$, which may be the same or different, each represents: a hydrogen atom; a linear or branched alkyl group containing from 1 to 6 carbon atoms and optionally substituted by at least one halogen atom, hydroxy or alkoxy group containing from 1 to 6 carbon atoms; an alkylaminoalkyl or dialkylaminoalkyl group wherein each alkyl group contains from 1 to 6 carbon atoms, or R$_2$ and R'$_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group 'c' defined above, and wherein, when there is more than one substituent, said substituent is the same or different, R$_3$ represents a group of formula:

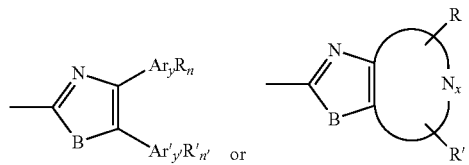

in which B represents an oxygen atom or a sulphur atom, x is 0, 1 or 2, y and y' are the same or different, and each is 0 or 1, Ar and Ar' are the same or different and each represents an aryl or heteroaryl group, n and n' are the same or different, and each is 1, when the y or y' with which it is associated is 0, or is equal to the number of positions that can be substituted on the associated Ar or Ar' when the said y or y' is 1, the fused ring containing N$_x$ is a five- or six-membered heteroaryl ring, and wherein R and R', which may be the same or different, each represent a hydrogen atom or a substituent selected from the group a, wherein the group a consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkoxy groups; aryloxy groups; alkoxycarbonyl; aralkoxycarbonyl; aryloxycarbonyl; hydroxycarbonylalkyl; alkoxycarbonylalkyl; aralkoxycarbonylalkyl; aryloxycarbonylalkyl; perfluoroalkyl; perfluoroalkoxy; —CN; acyl; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonyl-amino, fluoroalkylcarbonylamino, or diacylamino group; CONH$_2$; alkyl-, aralkyl-, and aryl-amido groups; alkylthio, arylthio and aralkylthio and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino; and saturated and unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; CONH$_2$; alkylamido groups; alkylthio and the oxidised sulphoxide and sulphone forms thereof; sulphonyl, alkylsulphonyl groups; and sulphonamide, alkylsulphonamide, and di(alkylsulphonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group.

In one aspect, the calcimimetic compound can be 3-(1,3-benzothiazol-2-yl)-1-(3,3-diphenylpropyl)-1-(2-(4-morpholinyl)ethyl)urea or pharmaceutically acceptable salt thereof. In another aspect, the calcimimetic compound can be N-(4-(2-((((3,3-diphenylpropyl)(2-(4-morpholinyl)ethyl)amino)carbonyl)amino)-1,3-thiazol-4-yl)phenyl)methanesulfonamide or pharmaceutically acceptable salt thereof.

In one aspect, the calcimimetic compound of the invention can be chose from compounds of Formula V

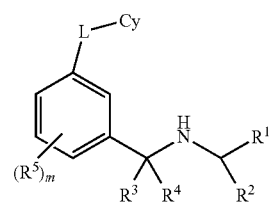

wherein:

R$^1$ is phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from C$_{1-6}$alkyl, halogen, C$_{1-4}$haloalkyl, —OC$_{1-6}$alkyl, cyano and nitro;

R$^2$ is C$_{1-8}$alkyl or C$_{1-4}$haloalkyl;

R$^3$ is H, C$_{1-4}$haloalkyl or C$_{1-8}$alkyl;

R$^4$ is H, C$_{1-4}$haloalkyl or C$_{1-8}$alkyl;

R$^5$ is, independently, in each instance, H, C$_{1-8}$alkyl, C$_{1-4}$haloalkyl, halogen, —OC$_{1-6}$alkyl, —NR$^a$R$^d$, NR$^a$C(=O)R$^d$, substituted or unsubstituted pyrrolidinyl, substituted or unsubstituted azetidinyl, or substituted or unsubstituted piperidyl, wherein the substituents can be selected from halogen, —OR$^b$, —NR$^a$R$^d$, —C(=O)OR$^c$, —C(=O)NR$^a$R$^d$, —OC(=O)R$^c$, —NR$^a$C(=O)R$^c$, cyano, nitro, —NR$^a$S(=O)$_n$R$^c$ or —S(=O)$_n$NR$^a$R$^d$;

L is —O—, —OC$_{1-6}$alkyl-, —C$_{1-6}$alkylO—, —N(R$^a$)(R$^d$)—, —NR$^a$C(=O)—, —C(=O)—, —C(=O)NR$^d$C$_{1-6}$alkyl-, —C$_{1-6}$alkyl-C(=O)NR$^d$—, —NR$^d$C(=O)NR$^d$—, —NR$^d$C(=O)NR$^d$C$_{1-6}$alkyl-, —NR$^a$C(=O)R$^c$—, —NR$^a$C(=O)OR$^c$—, —OC$_{1-6}$alkyl-C(=O)O—, —NR$^d$C$_{1-6}$alkyl-, —C$_{1-6}$alkylNR$^d$—, —S—, —S(=O)$_n$—, —NR$^a$S(=O)$_n$, or —S(=O)$_n$N(R$^a$)—;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of R$^6$, C$_{1-8}$alkyl, C$_{1-4}$haloalkyl, halogen, cyano, nitro, —OC$_{1-6}$alkyl, —NR$^a$R$^d$, NR$^d$C(=O)R$^d$, —C(=O)OR$^c$, —C(=O)NR$^a$R$^d$, —OC(=O)R$^c$, —NR$^a$C(=O)R$^c$, —NR$^a$S(=O)$_m$R$^c$ or —S(=O)$_m$NR$^a$R$^d$;

R$^6$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of C$_{1-8}$alkyl, C$_{1-4}$haloalkyl, halogen, cyano, nitro, —OC$_{1-6}$alkyl, —NR$^a$R$^d$, NR$^d$C(=O)R$^d$, —C(=O)OR$^c$, —C(=O)NR$^a$R$^d$, —OC(=O)R$^c$, —NR$^a$C(=O)R$^c$, —NR$^a$S(=O)$_m$R$^c$ or —S(=O)$_m$NR$^a$R$^d$;

R$^a$ is, independently, at each instance, H, C$_{1-4}$haloalkyl, C$_{1-6}$alkyl, C$_{1-6}$alkenyl, C$_{1-6}$alkylaryl or arylC$_{1-6}$alkyl:

R$^b$ is, independently, at each instance, C$_{1-8}$alkyl, C$_{1-4}$haloalkyl, phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from C$_{1-6}$alkyl, halogen, C$_{1-4}$haloalkyl, —OC$_{1-6}$alkyl, cyano and nitro;

R$^c$ is, independently, at each instance, C$_{1-6}$alkyl, C$_{1-4}$haloalkyl, phenyl or benzyl;

R$^d$ is, independently, at each instance, H, C$_{1-6}$alkyl, C$_{1-6}$alkenyl, phenyl, benzyl, naphthyl or a saturated or unsaturated 5- or 6-membered heterocycle ring containing 1, 2 or 3 atoms selected from N, O and S, with no more than 2 of the atoms selected from O and S, wherein the C$_{1-6}$alkyl, phenyl, benzyl, naphthyl and heterocycle are substituted by 0, 1, 2, 3 or 4 substituents selected from C$_{1-6}$alkyl, halogen, C$_{1-4}$haloalkyl, —OC$_{1-6}$alkyl, cyano and nitro, R$^b$, —C(=O)R$^c$, —OR$^b$, —NR$^a$R$^b$, —C(=O)OR$^c$, —C(=O)NR$^a$R$^b$, —OC(=O)R$^c$, —NR$^a$C(=O)R$^c$, —NR$^a$S(=O)$_m$R$^c$ and —S(=O)$_m$NR$^a$R$^c$;

m is 1 or 2;

n is 1 or 2;

provided that if L is —O— or —OC$_{1-6}$alkyl-, then Cy is not phenyl.

In one aspect, the calcimimetic compound can be N-(2-chloro-5-((((1R)-1-phenylethyl)amino)methyl)phenyl)-5-methyl-3-isoxazolecarboxamide or a pharmaceutically acceptable salt thereof. In another aspect, the calcimimetic compound can be N-(2-chloro-5-((((1R)-1-phenylethyl)amino)methyl)phenyl)-2-pyridinecarboxamide or a pharmaceutically acceptable salt thereof.

Calcimimetic compounds useful in the methods of the invention include the calcimimetic compounds described above, as well as their stereoisomers, enantiomers, polymorphs, hydrates, and pharmaceutically acceptable salts of any of the foregoing.

B. Methods of Assessing Calcimimetic Activity

In one aspect, compounds binding at the CaSR-activity modulating site can be identified using, for example, a labeled compound binding to the site in a competition-binding assay format.

Calcimimetic activity of a compound can be determined using techniques such as those described in International Publications WO 93/04373, WO 94/18959 and WO 95/11211.

Other methods that can be used to assess compounds calcimimetic activity are described below.

HEK 293 Cell Assay

HEK 293 cells engineered to express human parathyroid CaSR (HEK 293 4.0-7) have been described in detail previously (Nemeth E F et al. (1998) Proc. Natl. Acad. Sci. USA 95:4040-4045). This clonal cell line has been used extensively to screen for agonists, allosteric modulators, and antagonists of the CaSR (Nemeth E F et al. (2001) J. Pharmacol. Exp. Ther. 299:323-331).

For measurements of cytoplasmic calcium concentration, the cells are recovered from tissue culture flasks by brief treatment with 0.02% ethylenediaminetetraacetic acid (EDTA) in phosphate-buffered saline (PBS) and then washed and resuspended in Buffer A (126 mM NaCl, 4 mM KCl, 1 mM CaCl$_2$, 1 mM MgSO$_4$, 0.7 mM K$_2$HPO$_4$/KH$_2$PO$_4$, 20 mM Na-Hepes, pH 7.4) supplemented with 0.1% bovine serum albumin (BSA) and 1 mg/ml D-glucose. The cells are loaded with fura-2 by incubation for 30 minutes at 37° C. in Buffer A and 2 μM fura-2 acetoxymethylester. The cells are washed with Buffer B (Buffer B is Buffer A lacking sulfate and phosphate and containing 5 mM KCl, 1 mM MgCl$_2$, 0.5 mM CaCl$_2$ supplemented with 0.5% BSA and 1 mg/ml D-glucose) and resuspended to a density of 4 to 5×10$^6$ cells/ml at room temperature. For recording fluorescent signals, the cells are diluted five-fold into prewarmed (37° C.) Buffer B with constant stirring. Excitation and emission wavelengths are 340 and 510 nm, respectively. The fluorescent signal is recorded in real time using a strip-chart recorder.

For fluorometric imaging plate reader (FLIPR) analysis, HEK 293 cells are maintained in Dulbecco's modified Eagle's medium (DMEM) with 10% fetal bovine serum (FBS) and 200 μg/ml hygromycin. At 24 hrs prior to analysis, the cells are trypsinized and plated in the above medium at 1.2×10$^5$ cells/well in black sided, clear-bottom, collagen 1-coated, 96-well plates. The plates are centrifuged at 1,000 rpm for 2 minutes and incubated under 5% CO$_2$ at 37° C. overnight. Cells are then loaded with 6 μM fluo-3 acetoxymethylester for 60 minutes at room temperature. All assays are performed in a buffer containing 126 mM NaCl, 5 mM KCl, 1 mM MgCl$_2$, 20 mM Na-Hepes, supplemented with 1.0 mg/ml D-glucose and 1.0 mg/ml BSA fraction IV (pH 7.4).

In one aspect, the EC$_{50}$'s for the CaSR-active compounds can be determined in the presence of 1 mM Ca$^{2+}$. The EC$_{50}$ for cytoplasmic calcium concentration can be determined starting at an extracellular Ca$^{2+}$ level of 0.5 mM. FLIPR experiments are done using a laser setting of 0.8 W and a 0.4 second CCD camera shutter speed. Cells are challenged with calcium, CaSR-active compound or vehicle (20 μl) and fluorescence monitored at 1 second intervals for 50 seconds. Then a second challenge (50 μl) of calcium, CaSR-active compound, or vehicle can be made and the fluorescent signal monitored. Fluorescent signals are measured as the peak height of the response within the sample period. Each response is then normalized to the maximum peak observed in the plate to determine a percentage maximum fluorescence.

Bovine Parathyroid Cells

The effect of calcimimetic compounds on CaSR-dependent regulation of PTH secretion can be assessed using primary cultures of dissociated bovine parathyroid cells. Dissociated cells can be obtained by collagenase digestion, pooled, then resuspended in Percoll purification buffer and purified by centrifugation at 14,500×g for 20 minutes at 4° C. The dissociated parathyroid cells are removed and washed in a 1:1 mixture of Ham's F-12 and DMEM (F-12/DMEM) supplemented with 0.5% BSA, 100 U/ml penicillin, 100 μg/ml streptomycin, and 20 μg/ml gentamicin. The cells are finally resuspended in F-12/DMEM containing 10 U/ml penicillin, 10 μg/ml streptomycin, and 4 μg/ml gentamicin, and BSA was substituted with ITS+ (insulin, transferrin, selenous acid, BSA, and linoleic acid; Collaborative Research, Bedford, Mass.). Cells are incubated in T-75 flasks at 37° C. in a humidified atmosphere of 5% $CO_2$ in air.

Following overnight culture, the cells are removed from flasks by decanting and washed with parathyroid cell buffer (126 mM NaCl, 4 mM KCl, 1 mM $MgSO_4$, 0.7 mM $K_2HPO_4$/$KH_2PO_4$, 20 mM Na-Hepes, 20; pH 7.45 and variable amounts of $CaCl_2$ as specified) containing 0.1% BSA and 0.5 mM $CaCl_2$. The cells are resuspended in this same buffer and portions (0.3 ml) are added to polystyrene tubes containing appropriate controls, CaSR-active compound, and/or varying concentrations of $CaCl_2$. Each experimental condition is performed in triplicate. Incubations at 37° C. are for 20 minutes and can be terminated by placing the tubes on ice. Cells are pelleted by centrifugation (1500×g for 5 minutes at 4° C.) and 0.1 ml of supernatant is assayed immediately. A portion of the cells is left on ice during the incubation period and then processed in parallel with other samples. The amount of PTH in the supernatant from tubes maintained on ice is defined as "basal release" and subtracted from other samples. PTH is measured according to the vendor's instructions using rat PTH-(1-34) immunoradiometric assay kit (Immunotopics, San Clemente, Calif.).

MTC 6-23 Cell Calcitonin Release

Rat MTC 6-23 cells (clone 6), purchased from ATCC (Manassas, Va.) are maintained in growth media (DMEM high glucose with calcium/15% HIHS) that is replaced every 3 to 4 days. The cultures are passaged weekly at a 1:4 split ratio. Calcium concentration in the formulated growth media is calculated to be 3.2 mM. Cells are incubated in an atmosphere of 90% $O_2$/10% $CO_2$, at 37° C. Prior to the experiment, cells from sub-confluent cultures are aspirated and rinsed once with trypsin solution. The flasks are aspirated again and incubated at room temperature with fresh trypsin solution for 5-10 minutes to detach the cells. The detached cells are suspended at a density of $3.0 \times 10^5$ cells/mL in growth media and seeded at a density of $1.5 \times 10^5$ cells/well (0.5 mL cell suspension) in collagen-coated 48 well plates (Becton Dickinson Labware, Bedford, Mass.). The cells are allowed to adhere for 56 hours post-seeding, after which the growth media was aspirated and replaced with 0.5 mL of assay media (DMEM high glucose without/2% FBS). The cells are then incubated for 16 hours prior to determination of calcium-stimulated calcitonin release. The actual calcium concentration in this media is calculated to be less than 0.07 mM. To measure calcitonin release, 0.35 mL of test agent in assay media is added to each well and incubated for 4 hours prior to determination of calcitonin content in the media. Calcitonin levels are quantified according to the vendor's instructions using a rat calcitonin immunoradiometric assay kit (Immutopics, San Clemente, Calif.).

Inositol Phosphate Assay

The calcimimetic properties of compounds could also be evaluated in a biochemical assay performed on Chinese hamster ovarian (CHO) cells transfected with an expression vector containing cloned CaSR from rat brain [CHO(CaSR)] or not [CHO(WT)] (Ruat M., Snowman A M., J. Biol. Chem 271, 1996, p 5972). CHO(CaSR) has been shown to stimulate tritiated inositol phosphate ([$^3$H]IP) accumulation upon activation of the CaSR by $Ca^{2+}$ and other divalent cations and by NPS 568 (Ruat et al., J. Biol. Chem 271, 1996). Thus, [$^3$H]IP accumulation produced by 10 μM of each CaSR-active compound in the presence of 2 mM extracellular calcium can be measured and compared to the effect produced by 10 mM extracellular calcium, a concentration eliciting maximal CaSR activation (Dauban P. et al., Bioorganic & Medicinal Chemistry Letters, 10, 2000, p 2001).

C. Pharmaceutical Compositions and Administration

Calcimimetic compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see Berge et al. J. Pharm. Sci. 66: 1, 1977. In certain embodiments of the invention salts of hydrochloride and salts of methanesulfonic acid can be used.

In some aspects of the present invention, the calcium-receptor active compound can be chosen from cinacalcet, i.e., N-(1-(R)-(1-naphthyl)ethyl]-3-[3-(trifluoromethyl)phenyl]-1-aminopropane, cinacalcet HCl, and cinacalcet methanesulfonate. The calcimimetic compound, such as cinacalcet HCl and cinacalcet methanesulfonate, can be in various forms such as amorphous powders, crystalline powders, and mixtures thereof. The crystalline powders can be in forms including polymorphs, psuedopolymorphs, crystal habits, micromeretics, and particle morphology.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions).

The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, suppositories, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

In some aspects of the present invention, the compositions disclosed herein comprise a therapeutically effective amount of a calcium receptor-active compound for the treatment or prevention of bowel disorders. For example, in certain embodiments, the calcimimetic compound such as cinacalcet HCl can be present in an amount ranging from about 1% to about 70%, such as from about 5% to about 40%, from about 10% to about 30%, or from about 15% to about 20%, by weight relative to the total weight of the composition.

The compositions useful in the invention may contain one or more active ingredients in addition to the calcium sensing receptor-active compound. The additional active ingredient may be another calcimimetic compound, or it may be an active ingredient having a different therapeutic activity. Examples of such additional active ingredients include vitamins and their analogs, such as antibiotics, lanthanum carbonate, anti-inflammatory agents (steroidal and non-steroidal) and inhibitors of pro-inflammatory cytokine (ENBREL®, KINERET®). When administered as a combination, the therapeutic agents can be formulated as separate compositions that are given at the same time or different times, or the therapeutic agents can be given as a single composition.

In one aspect, the pharmaceutical compositions useful for methods of the invention may include additional compounds as described in more detail below.

In another aspect, the compounds used to practice the methods of the instant invention can be formulated for oral administration that release biologically active ingredients in the colon without substantial release into the upper gastrointestinal tract, e.g. stomach and intestine. Oral delivery of drugs to the colon can allow achieving high local concentration while minimizing side effects that occur because of release of drugs in the upper GI tract or unnecessary systemic absorption. The advantage of colonic delivery of drugs can be due to the fact that poorly absorbed drugs may have an improved bioavailability, colon is somewhat less hostile environments with less diversity and intensity of activity that the stomach and small intestine, and the colon has a longer retention time and appears highly responsive to agents that enhance the absorption of poorly absorbed drugs. Chourasia, M. et al. (2003) *J. Pharm. Pharmaceut. Sci* 6(1): 33-66. Some pharmaceutical approaches that can be used for the development if colon targeted drug delivery systems are summarized in Table 1.

TABLE 1

| Approach | Basic Features |
|---|---|
| Covalent linkage of a drug and a carrier | |
| Azo conjugates | The drug is conjugated with an azo bond |
| Cyclodextrin conjugates | The drug is conjugated with cyclodextrin |
| Glycoside conjugates | The drug is conjugated with glycisode |
| Glucoronate conjugates | The drug is conjugated with glucoronate |
| Dextran conjugates | The drug is conjugated with dextran |
| Polypetide conjugates | The drug is conjugated with poly(aspartic acid) |

TABLE 1-continued

| Approach | Basic Features |
|---|---|
| Approaches to deliver the intact molecule to the colon | |
| Coating with pH-sensitive polymers | Formulation coated with enteric polymers releases drug when pH moves towards alkaline range |
| Coating with biodegradable polymers | Drug is released following degradation of the polymer due to the action of colonic bacteria |
| Embedding in biodegradable matrices and hydrogels | The embedded drug in polysaccharide matrices is released by swelling and by the biodegradable action of polysaccharidases |
| Embedding in pH-sensitive matrices | Degradation of the pH-sensitive polymer in the GI tract releases the embedded drug |
| Time released systems | Once the multicoated formulation passes the stomach, the drug is released after a lag time of 3-5 h that is equivalent to small intestine transit time |
| Redox-sensitive polymers | Drug formulated with azo polymer and disulfide polymers that selectively respond to the redox potential of the colon provides colonic delivery |
| Bioadhesive systems | Drug coated with a bioadhesive polymer that selectively provides adhesion to the colonic mucosa may release drug in the colon |
| Coating with microparticles | Drug is linked with microparticles |
| Osmotic controlled drug delivery | Drug is released through semipermeable membrane due to osmotic pressure |
| Suppositories | Drug is released from microscopic polymeric particles wherein drug is homogeneously incorporated within a pharmaceutically acceptable suppository base. |

In another example, pharmaceutical compositions of the invention can be used with the drug carrier including pectin and galactomannan, polysaccharides that are both degradable by colonic bacterial enzymes (U.S. Pat. No. 6,413,494). While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

III. Methods of Treatment

In one aspect, the invention provides methods for treatment of bowel disorders. In one aspect, bowels disorders include inflammatory bowel disease. In another aspect, bowel disorders include irritable bowel syndrome. In a further aspect, bowel disorders include diverticular disease, collagenous and lymphatic colitis, diversion colitis, endometriosis, typhlitis, colitis, cystica profunda, pneumatosis cystoides intestinalis, or malakoplakia.

A. IBD

In one aspect, the present invention provides method of treatment or prevention of inflammatory bowel disease. Inflammatory bowel disease, or IBD, as used herein, is a disease characterized by inflammation or ulcerations in the small and/or large intestine with chronically recurring symptoms of abdominal pain and alteration in bowel habits. IBD has been classified into the broad categories of Chron's disease (CD) and ulcerative colitis (UC). Though patients with CD and UC may present with similar symptoms such as diarrhea and abdominal pain, the characteristic differences are listed in Table 2.

TABLE 2

| Feature | Ulcerative Colitis | Chron's disease |
|---|---|---|
| Distribution | Affects only colon | Can affect the entire digestive tract, although more likely to affect proximal intestine |
| Pattern of inflammation | Continuous | Patchy in spots of ulceration and normal tissue called "skips" |
| Depth of inflammation | Mucosal disease (shallow ulcers) | Transmural disease (deep ulcers) |
| Signs and symptoms | Rectal bleeding, diarrhea, tenesmus, abdominal pain (rectal bleeding always present) | Diarrhea, abdominal pain, weight loss. Can be associated with strictures, fistulas, granulomas and perianal sores (rectal bleeding may occur) |

In one aspect, the invention provides methods for treating UC using calcimimetic compounds and compositions. In another aspect, the methods of the invention can be used for treatment of CD using calcimimetic compounds and compositions. In one aspect, methods of the present invention result in prevention of onset or alleviation of one or more signs or symptoms of UC or CD. Table 3 further summarizes inflammatory markers in pathophysiology of IBD and signs/symptoms commonly found in ulcerative colitis and Chron's disease.

TABLE 3

| Sign/Symptom | Ulcerative Colitis | Chron's Disease |
| --- | --- | --- |
| Area of intestinal tract affected | Any part of innermost lining of colon, continuous with no patches of normal tissues | Lower ileum most common but can flare up anywhere, including the colon, patches of normal tissue between affected areas; can affect entire intestinal wall |
| Diarrhea | Typically four episodes per day | Typically four episodes per day |
| Abdominal pain/cramping | Mild tenderness, lower abdominal cramping | Moderate to severe abdominal tenderness in right lower quadrant |
| Blood in stool | Present; amount depends on disease severity | May be present; amount depends on disease severity |
| Fatigue | Result of excessive blood loss and anemia | Result of excessive blood loss, anemia, and poor nutrient absorption |
| Fever | Low-grade in severe cases | Low-grade in severe cases |
| Physical examination | Rectal exam may show perianal irritation, fissures, hemorrhoids, fistulas, and abscesses | Peritoneal irritation, abdominal or pelvis mass |
| Weight loss/anorexia | Weight loss in more severe cases | Weight loss and anorexia common due to poor digestion and intestinal absorption |
| Appetite | Often decreased during periods of disease exacerbation | Often decreased during periods of disease exacerbation |
| Risk of colon cancer | Increased | Increased |

To diagnose IBD, a careful medical history is taken, including details and durations of symptoms, and whether there is a family history of IBD or cigarette smoking history. Next, blood tests can help detect anemia, high white cell counts (indicating inflammation or infection), and low nutrient levels. Stool samples can rule out intestinal infection which can lead to similar symptoms as IBD. The diagnosis of IBD is established by finding characteristic changes in the lining of the intestinal tract by endoscopy and characteristic histological features on biopsy, which can be obtained via endoscopy. X-ray examinations such as double-contrast barium enemas or oral barium with small bowel follow-through ("upper GI series") are used to confirm the diagnosis following endoscopy and examine the extent of mucosal disease. CT or MRI scans are occasionally ordered to look for complications of IBD, such as obstruction. Current area of investigation includes genetic testing and video capsule endoscopy. In wireless capsule endoscopy, a pill is swallowed and travels through the small intestine taking pictures that are transmitted to a recorder and later viewed on a computer. This test is more sensitive for CD in the small intestine than X-rays.

In one aspect, the invention provides methods for treating mild IBD. In another aspect, the invention provides methods for treating moderate IBD. In a further aspect, the invention provides methods for treating severe IBD. The severity of inflammatory bowel disease is characterized in Table 4.

TABLE 4

| | Mild | Moderate | Severe |
| --- | --- | --- | --- |
| Ulcerative colitis | Fewer than 4 stools daily Intermittent bleeding Normal hematocrit and erythrocyte sedimentation rate (ESR) levels | 4 to 6 stools daily Frequent bleeding Hematocrit of 20 to 30% ESR of 20 to 30 mm/h | More than 6 bloody stools daily Hematocrit of less than 30% Weight loss greater than 10% ESR > 30 mm/h |
| Chron's disease | No dehydration or obstruction Weight loss < 10% | Fever Anemia Weight loss > 10% | Fever Obstruction Abscess |

In one aspect, methods of the present invention can be practiced in combination with nutritional management. Deficiencies of specific nutrients in IBD can be managed by supplementation. For example, calcimimetic compounds and compositions can be administered in combination with calcium, magnesium, zinc, iron, folate, vitamin $B_{12}$, vitamin D, or vitamin K. In another example, compound and compositions of the invention can be administered concurrently with cholestyramine therapy. In one aspect, compounds and compositions of the invention can be administered with antidiarrheal agents, antispasmodics or anticholinergics, or analgesics. Examples of antidiarrheal agents include loperamide or diphenoxylate. Examples of anticholinergics include belladonna, clidinium, propantheline bromides, and dicyclomine hydrochloride. An analgesic can be chosen based on the disease severity. In one aspect, compounds and compositions of the invention can be administered together with 5-aminosalicylic acid compounds (5-ASA). Examples of 5-ASA preparations include mesalamine (5-ASA) suppositories, 5-ASA enemas, sulfasalazine, asacol, pentasa, dipentum and colazol. In another aspect, compounds and compositions of the invention can be administered concurrently with steroids, such as cortisone, corticosteroid enemas, budesonide, or prednisone. In a further aspect, compounds and compositions of the invention can be administered together with immunomodulators (i.e., drugs that act by blocking lymphocyte proliferation, activation, or effector mechanisms). Examples of immunomodulators include 6-mercaptopurine (6-MP), azathioprine, methotrexate, cyclosporine, or anti-TNF antibodies such as infliximab (Remicade®) or CDP571 (humanized IgG4 antibody against TNF-α). In another aspect of the invention, compounds and compositions of the invention can be administered concurrently with antibiotics, such as metronidazole or ciproflaxin. In one aspect, compounds and compositions of the invention can be administered concurrently with Humira®. In another aspect, compounds and compositions of the invention can be administered together with CNTO-1275 (Centocor). In a further aspect, compounds and compositions of the invention can be administered concurrently with Basiliximab (Simulect), FK506 or sargramostim.

In one aspect, compounds and compositions of the invention can be administered in conjunction with surgical treatments. In another aspect, calcimimetic compounds and compositions of the invention can be administered concurrently with treatment involving recombinant cytokines or antibodies to cytokines. In one aspect, a combination therapy may include recombinant IL-10. In another aspect, calcimimetic compounds and compositions of the invention can be used concurrently with probiotics. In a further aspect, the calcimimetic compounds of the present invention can be administered together with compounds or treatments that block the proinflammatory properties of CpG motifs, such as CpG-ODN or AV-ODN (See Obermeier, F. et al. (2005) *Gastroenterology* 129: 913-927; Obermeier, F. et al. (2005) *Gut* 54: 1428-1436). In another aspect, calcimimetic compounds and compositions of the invention can be used with heparin, lidocaine, or rosiglitazone.

B. IBS

In one aspect, the present invention provides method of treatment or prevention of irritable bowel syndrome. Irritable bowel syndrome, or IBS, as used herein, is a gastrointestinal disorder characterized by altered bowel habits and abdominal pain, typically in the absence of detectable structural abnormalities or biochemical cause. The Rome II criteria can be used to diagnose IBS and rule out other disorders. The criteria include at least 3 months of the following continuous recurrent symptoms: abdominal pain or discomfort that is relieved by defecation or is associated with a change in the frequency or consistency of stool, and disturbed defecation involving two or more of the following characteristics at least 25% of the time: altered stool frequency, altered stool form (e.g., lumpy or hard, or loose or watery), altered stool passage (e.g., straining, urgency, or feeling of incomplete evacuation), passage of mucus, bloating or feeling of abdominal distention. The intensity and location of abdominal pain in IBS can be highly variable, even within an individual patient: it is localized to the hypogastrium in 25%, the right side in 20%, the left side in 20%, and the epigastrium in 10% of the patients. The pain can be generally crampy or achy, although sharp, dull, gas-like, or non-descript pains are also common. In one aspect, patients with IBS may present with constipation (IBS-C, constipation predominant IBS), diarrhea (IBS-D, diarrhea-predominant IBS), or constipation alternating with diarrhea (IBS-A, mixed symptom IBS, or "alternators"). Long period of straining may be required for fecal evaluation both in constipation- and diarrhea-predominant patient. Constipation may persist for weeks to months, interrupted by brief periods of diarrhea. Feelings of incomplete fecal evacuation may lead to multiple attempts at stool passage daily. In patients with IBS-D, stools are characteristically loose and frequent but of normal daily volume. Mucus discharge has been reported in up to 50% of patients with IBS. Upper gut symptoms are common in IBS, with 25% to 50% of patients reporting heartburn, early satiety, nausea, and vomiting, up to 87% note intermittent dyspepsia. Agreus L. et al. (1995) *Gastroenterology* 109: 671. Extraintestinal complaints in patients with IBS include chronic pelvic pain, fibromyalgia, genitourinary dysfunctions, such as dysmenorrheal, dyspareunia, impotence, urinary frequency, nocturia, and a sensation of incomplete bladder emptying. Impaired sexual function is reported by 83% of patients with IBS. Patients with functional bowel disorders have higher incidences of hypertension, headaches, peptic ulcer disease, rashes than the general population and more commonly report fatigue, loss of concentration, insomnia, palpitations, and unpleasant tastes in the mouth.

While the pathogenesis of IBS is poorly understood, it has been proposed that abnormal gut motor and sensory activity, central neural dysfunction, psychological disturbances, stress and luminal factors play a role. IBS has been associated with colonic and small intestinal motility abnormalities, as well as with motor abnormalities in other smooth muscle sites. The visceral sensory abnormalities, which may be responsible for sensations of pain, gas, or bloating in IBS, have been a major focus of investigation. Perception of abdominal symptoms is mediated by afferent neural pathways which are activated by visceral stimuli acting on chemoreceptors, mechanoreceptors, and receptors in the mesentery which may play a role in painful stimulation of the gut. Information from these activated receptors is carried in spinal afferent nerves and thus transmitted to the brain where conscious perception occurs. It is postulated that IBS results from sensitization of afferent pathways such that normal physiological gut stimuli not perceived by healthy individuals induce pain in the patient with IBS. The sensitizing event responsible for induction of symptoms in IBS is unknown. The clinical association of emotional disorders and stress with symptom exacerbation and the therapeutic response to therapies that act on cerebral cortical sites strongly suggests the role of central nervous system factors in the pathogenesis of IBS. However, it is unclear whether IBS represents a primary gut disturbance with inappropriate input from the central nervous system or a central nervous system disorder with centrally directed changes in gut motor and sensory activity. Further, both mental stress and administration of the cholinesterase inhibitor neostigmine evoke increases in colonic motility and changes in electroencephalographic waveforms which are exaggerated in patients with IBS compared to healthy volunteers, suggesting that both the gut and brain are hypersensitive in IBS. Investigations of the effects of stress reinforce the importance of the brain-gut axis in the regulation of colonic activities. A strongly positive relationship has been reported between daily stress and daily symptoms in women with IBS. Levy R. et al. (1997) *J. Behav. Med.* 20: 177.

In one aspect, the methods of the invention can be practiced concurrently with dietary modifications. These modifications can include, for example, limiting fat intake or restricting intake of poorly digestible sugars such as fructose and sorbitol, or exclusion or limiting of foods associated with increased flatulence, e.g., beans, onions, celery, carrots, raisins, bananas, apricots, prunes, brussel sprouts, pretzels, wheat germ, and bagels. In one aspect, the modifications may include increased fiber intake. Fiber supplements can include bran, Metamucil, psyllium, process flea seed husk (ispaghula), and calcium polycarbophyl. In another aspect, probiotics can be used to repopulate the gut with good bacteria.

Compounds and compositions of the present invention can be administered together with other medical treatments. In one aspect, for patients with constipation-predominant IBS, osmotic laxatives can be used to effect defecation. These laxatives include hypertonic salt solution such as milk of magnesia, poorly absorbable sugars such as lactulose and sorbitol, and isotonic electrolyte solutions containing polyethylene glycol. For diarrhea-predominant IBS, opiate-based agents can be used, such as loperamide, Imodium, bile acid-sequestering drugs, acid-suppressing drugs in the $H_2$ receptor agonist and proton pump inhibitor classes. For pain-predominant IBS, methods of the invention can be practiced together with co-administration of anti-spasmodic agents, such as drugs that block cholinergic nerve function (e.g., dicyclomine, prifinium, cimetropiuim, zamifenacin), agents that prevent calcium flux (e.g., dilatiazem, pinaverium, octylonium, peppermint oil), and direct gut smooth muscle relaxants, as well as agents that act via unknown pathways. Other antispasmodics include mebeverine and trimebutine. In another aspect, compounds and compositions of the invention can be used in the treatment of IBS with anti-depressant agents, for example, agents in the tricyclic class, such as amitriotyline, trimipramine, desipramine, nortriotyline, fluphenazine; the selective serotonin reuptake inhibitors, e.g., paroxetine, citalopram, mianserin; or serotonin receptor antagonists, e.g., ondansertron, graniseton, alosertron, or $5HT_4$ receptor antagonist SB-207266-A.

In one aspect, the invention provides methods for treating IBS in conjunction with other medications, for example, prokinetic medications, such as tegaserod, peripheral dopamine receptor antagonists, such as domperidone; hormonal treatments (for example, gonadotropin-releasing hormone, such as leuprolide; tranquilizers, such as phenaglycodol, meprobamate, heteronium plus amobarbital, propantheline plus phenobarbital, chlordiazepoxide, diazepam, medazepam, and alprazolam. In another aspect, the invention provides methods for treating IBS in conjunction with other medications, such as agents that blunt visceral hyperalgesia in IBS, for example, kappa-opioid compounds, $\alpha_2$-adrenoceptor agonists (e.g., yohimbine, lidamidine), neurokinin-1 ($NK_1$) receptor antagonists, somatostatin analogs (e.g., octreotide), or oxytocin. In a further aspect, methods of the invention can be practiced in conjunction with psychological therapy, cognitive therapy, biofeedback and stress reduction techniques, and hypnosis. In one aspect, compounds and compositions of the invention can be used in conjunction with itopride, saredutant, renzapride, lubiprostone, or dynogen.

C. Other Bowel Disorders

The invention further provides methods for using calcimimetic compounds and compositions of the invention for treatment of colitis, e.g., collagenous and lymphocytic colitis, disorders characterized by chronic watery diarrhea with normal endoscopic and radiographic evaluations but histological evidence of chronic mucosal inflammation. In other aspect, the compounds and compositions of the invention can be used for treatment of diversion colitis, endometriosis, typhlitis, colitis, cystica profunda, pneumatosis cystoides intestinalis, and malakoplakia. Clinical and pathological characteristics of these and other inflammatory disorders of the colon that can be treated using the methods of the invention are summarized in Table 5.

TABLE 5

| Condition | Primary Location | Symptoms | Endoscopic Findings | Histological Findings |
|---|---|---|---|---|
| Lymphocytic colitis | Diffuse | Diarrhea | Normal | Mucosal inflammation with mononuclear cells, increased intraepithelial lymphocytes, few neutrophils |
| Collagenous colitis | Diffuse | Diarrhea | Normal | Similar to above, plus subepithelial collagen band > 10 μm |
| Diversion colitis | Bypassed segment | Mucoid discharge, bleeding | Erythema, granularity, friability | Follicular lymphoid hyperplasia, neutrophilic and mononuclear infiltration |
| Endometriosis | Rectosigmoid | Dysmenorrhea, dyspareunia, partial obstruction, rare hematochezia | Usually normal, rare extrinsic compression | Serosal implants of endometrial cells, muscular hypertrophy, fibrosis |
| Caustic enema-induced colitis | Rectosigmoid | Hematochezia, pain, diarrhea | Diffuse distal mucosal injury | Necrosis, ranging from epithelial to transmural, acute injury |
| Drug-induced ischemic colitis | Splenic flexure, descending | Pain, diarrhea, hematochezia | Friability, granularity, necrosis | Necrosis, acute inflammation |
| NSAID-induced ulcers | Diffuse, esp. rectosigmoid | Diarrhea, bleeding | Erythema, discrete ulcers | Acute and chronic inflammation, discrete ulcers |
| Nonspecific ulcers | Cecum, ascending colon | Pain, bleeding | Solitary, round ulcer | Acute and chronic inflammation |
| Stercoral ulcer | Rectosigmoid | Pain, bleeding, fever | Discrete ulcer, sharp margins | Transmural necrosis |
| Solitary rectal ulcer | Anterior rectum | Constipation, bleeding, pain | Demarcated ulcer | Fibromuscular obliteration of lamina propria |
| Typhilitis | Cecum | Pain, fever | Mucosal ulceration, | Mucosal necrosis, hemorrhage, |

TABLE 5-continued

| Condition | Primary Location | Symptoms | Endoscopic Findings | Histological Findings |
|---|---|---|---|---|
| | | | necrosis | submucosal edema, no inflammatory cells |
| Colitis cystica profunda | Anterior rectum | Bleeding, mucoid discharge | Polypoid submucosal mass, erythema, friability | Epithelial-lined cysts, fibrosis |
| Pneumatosis cystoides intestinalis | Idiopathic- left colon, secondary - right colon | None, rare pain | Multiple, soft, round submucosal masses | No epithelial lining, foreign-body giant cells, acute and chronic inflammation |
| Malakoplakia | Descending, rectosigmoid | None, diarrhea, pain, bleeding | Yellowish soft plaques of nodules | PAS-positive macrophages containing basophilic calculospherules |

The following examples are offered to more fully illustrate the invention, but are not to be construed as limiting the scope thereof.

EXAMPLE 1

This example outlines methods and techniques used in the present invention.

DSS Mouse and Rat Models of IBD

Animals. Female SJL/J mice aged 8-10 weeks were used for this study, purchased from Jackson Laboratories (Bar Harbour, Me.). Female Sprague-Dawley rats (approximately 150-300 grams) were purchased from Charles River Laboratories Inc. (Wilmington, Mass.). Mdr1a−/− mice (FVB.129P2-Abcb1a$^{tm1Bor}$N7), weight 20-21 g, 8 weeks at initiation of experiments, were housed and maintained (5 per cage) in the animal facility at Amgen Washington. All animals were cared for according to the standard protocols of the Amgen Institutional Animal Care and Use Committee.

Chemical reagents. Dextran sodium sulfate (DSS) with molecular mass 36-50 kDa was purchased from ICN Chemicals, Aurora, Ohio. The DSS solution was prepared as a 5% w/v solution in sterile water (Baxter Healthcare Corporation) and sterile filtered through a 0.45 μm filter before being added to drinking water. Water for the negative control groups was similarly filtered. FK506, (also known as Tacrolimus, active ingredient in Prograf®), chemical name [3S-[3R*[E(1S*, 3S*,4S*)],4S*,5R*,8S*,9E,12R*,14R*,15S*,16R*,18S*, 19S*,26aR*]]-5,6,8,11,12,13,14,15,16,17,18,19,24,25,26, 26a-hexadecahydro-5,19-dihydroxy-3-[2-(4-hydroxy-3-methoxycyclohexyl)-1-methylethenyl]-14,16-dimethoxy-4, 10,12,18-tetramethyl-8-(2-propenyl)-15,19-epoxy-3H-pyrodi[2,1-c][1,4]oxaazacyclotricosine-1,7,20,21(4H, 23H)-tetrone monohydrate, was used as a positive control for the inflammation treatment. Tacrolimus is a macrolide immunosuppressant produced by *Streptomyces tsukubaensis*. The solution of FK506 (Prograf®, Astellas) was prepared as follows: 0.1 mg/ml solution in phosphate buffered saline (PBS) was prepared by diluting 5 mg/ml stock solution. The animals were dosed with FK506 at 1 mg/kg in 200 μl of PBS.

The HEPES-Ringer solution contained (in mmol/L): NaCl 125; KCl 5; MgCl$_2$ 0.5; HEPES 22, CaCl$_2$ 0.1 or 1.6; glucose 10, pH 7.4. The solution was bubbled with 100% O$_2$. Tetrodotoxin (TTX) and Bumetanide (Bumet) was obtained from Sigma Chemical (St Louis, Mo., USA) and stock solutions were prepared in dimethyl sulphoxide (DMSO).

Calcimimetic solutions (Compound A, 3-(2-chlorophenyl)-N-((1R)-1-(3-(methyloxy)phenyl)ethyl)-1-propanamine, Compound B, (1R)-N-((6-(methyloxy)-4'-(trifluoromethyl)-3-biphenylyl)methyl)-1-phenylethanamine, Compound C, N-(2-chloro-5-((((1R)-1-phenylethyl)amino) methyl)phenyl)-5-methyl-3-isoxazolecarboxamide, and Compound D, N-(2-chloro-5-((((1R)-1-phenylethyl)amino) methyl)phenyl)-2-pyridinecarboxamide) were formulated and dosed in free base equivalents at volumes determined by the pharmacologist. Formulation vehicle was 20% (w/v) Captisol (β-Cyclodextrin Sulfobutyl Ether Sodium Salt, Research Grade from CyDex, Inc.) in water with a final pH of 2.0-2.2 at room temperature, adjusted with HCl and NaOH as required. Final concentrations of DMSO never exceeded 0.1% (v/v). Preliminary experiments indicated that the vehicle did not alter any baseline electrophysiological parameters.

DSS colitis in rats. All experiments were performed on groups of 6 male Sprague-Dawley rats, housed 2 per cage. For disease induction, rats were given 3% or 5% DSS ad libitum as drinking water for 8 days according to Okayasu, et al. (1990) *Gastroenterology* 98: 694-702. The DSS solution was prepared as a 3% w/v solution in sterile water for Irrigation, USP (Baxter Healthcare Corporation) and then sterile filtered through a 0.45 mm filter before being added to the sterile drinking bottle for the cage. The control water was similarly filtered and handled. Animals were administered either filtered drinking water or water containing 5% DSS for 8 days and the water in the drinking bottle was replaced from the stock solution every 3-4 days.

DSS colitis in mice. All experiments were performed on groups of 8 to 10 SJL-J mice, housed in the same cage. For disease induction, mice were given a 5% DSS ad libitum as drinking water for 9 days.

Postmortem evaluation. Mice and rats were euthanized by CO$_2$ asphyxiation. The large intestine were removed from the carcass, evaluated for gross lesions and three individual non-adjacent segments of proximal, middle and distal large intestine 2 centimeters long were immersed in the Zinc Formalin fix for 24 hours. At the end of 24 hours the sections were washed with tap water and put into 70% ethanol. Each section was then cut into three 3 mm pieces (9 pieces per animal), processed into paraffin blocks, and sections were cut in 5 μm sections and stained with hematoxylin and eosin.

In other sets of experiments, animals were anaesthetized by isofluorane inhalation and killed by cervical dislocation. Segments of distal colon between the $1^{st}$ and $2^{nd}$ distal lymph nodes were removed quickly, cut along the mesenteric border into a flat sheet and flushed with ice-cold basal HEPES-Ringer solution containing 0.1 mM Ca and Mg. Up to four of these unstripped colonic sheets were obtained from each animal.

Histomorphologic Examination

Histopathologic changes of the proximal, middle, and distal small and large intestine was scored as a global assessment of inflammation based on inflammatory infiltrate, edema, mucosal erosions or ulcerations as described in Table 6.

TABLE 6

| Grade | Inflammation | Comment |
|---|---|---|
| 0 | Absent | Normal |
| 1 | Minimal | Slight increase in cellularity (primarily lymphocytes in the laminia propria) |
| 2 | Mild | Increase in cellularity, neutrophils present, mild edema |
| 3 | Moderate | Diffuse increase in cellularity, focal erosions or ulcerations of mucosa, |
| 4 | Marked | Increased cellularity, Large and or multifocal mucosal ulcerations |
| 5 | Severe | Diffuse ulceration, loss mucosal architecture |

Calcium Diet

All experiments were performed on groups of 6 rats, housed 2 per cage. Animals were preloaded with a diet containing calcium at 2, 3, or 4% (normal diet contains 1.13% of calcium) for 2 weeks. For disease induction, rats were given a 5% DSS ad libitum as drinking water for 8 days beginning at the last day of the calcium preload. The calcium diet continued throughout the DSS phase of the study.

Nutrient Diets Formulations Containing an Amino Acid or Polyamine Agonist of the CaSR Sprague-Dawley rats were fed either a control "1% $Ca^{2+}$ diet" (Altromin, Germany; containing 0.95% (w/w) calcium, 0.2% (w/w) tryptophan; 0% (w/w) spermine) or a "high spermine diet" (Altromin, Germany; containing 0.95% (w/w) calcium and 0.1% (w/w) spermine) or a "high tryptophan diet" (Altromin, Germany; containing 0.95% (w/w) calcium, 1.0% (w/w) tryptophan; 0% (w/w) spermine) for 2 weeks before and also during the periods of DSS treatment.

Short-Circuit Current Measurement

Unstripped sheets from either proximal or distal colon were mounted between two halves of a modified Ussing chamber and short-circuited by a voltage clamp (VCC MC6; Physiologic Instruments) with correction for solution resistance. The exposure area was 0.3 $cm^2$ The mucosal and serosal surfaces of the tissue were bathed in reservoirs with 3-5 mL HEPES-Ringer solution, pH 7.4 (37° C.), maintained at 37° C. and continuously bubbled with 100% $O_2$. Tissues were allowed a minimum of 40-minute stabilization and basal recording period before drugs were added directly to the apical or basolateral side of the epithelium. Responses were recorded continuously and data were acquired via DATAQ™ instruments and were stored in a PC and processed using the program Acqualize™.

Statistical Analysis

The pathology scores (0, 1, 2, 3, 4 and 5) are treated as ordinal data in the analysis. Analyses of the comparisons of the calcimimetic (Compound A) vs Vehicle, calcimimetic (Compound A) vs FK 506, and FK 506 vs Vehicle were conducted separately in the following two fashions. The scores in the groups were compared at each location and across all location, treating the scores from three locations as repeated measures. The analysis for each location was conducted using Mantel-Haenszel Chi-square Exact test. The analysis of repeated measures was done using Generalize Estimating Equation (GEE). (Models for discrete longitudinal data; Geert Molenberghs and Geert Verbeke, Springer September 2005, Chapter 18.5).

Colitis in mdr1a−/− Mice

Induction of Colitis

Colitis was induced in female mdr1a$^{-/-}$ mice by infection with Helicobacter bilis via oral gavage. Mdr1a$^{-/-}$ mice (FVB.129P2-Abcb1a$^{tm1Bor}$N7) were obtained from Taconic (Hudson, N.Y.). These mice spontaneously develop colitis, but inoculation with H. bilis can induce a more robust colitis in a shorter timeframe with a higher frequency of disease. The protocol used in this study was modeled after the protocol described by Maggio-Price et al. in 2002 (Am J Pathol. 160 (2): 739-751).

H. bilis Culture and Infection

A frozen stock vial of H. bilis was thawed in a 1:1 mixture of brain heart infusion: Brucella broth and streaked onto blood agar plates. Plates were incubated for 2 days at 37° C. in a microaerobic chamber containing an atmosphere of 90% $N_2$, 5% $H_2$, and 5% $CO_2$. At the end of the 2 days of static growth, bacteria were harvested from the blood agar plate and placed into Erlenmeyer flasks containing Brucella broth supplemented with 5% FBS. This liquid culture was maintained with constant shaking for 24 hours at 37° C. in a microaerobic chamber. After liquid culture, the bacteria were concentrated by centrifugation and resuspended in Brucella broth. Bacteria were examined by gram stain for morphology, and other tests were run to confirm the presence of peroxidase, oxidase and urease activity. Bacterial concentration was determined by measuring the optical density at 600 nm (1 $OD_{600}$~$10^8$ CFU/mL). Bacteria were diluted to a concentration of $10^8$/mL, and 100 µL ($10^7$ bacteria) was orally gavaged to 40 mdr1a$^{-/-}$ mice. As a control, 5 mdr1a$^{-/-}$ mice were dosed with 100 µL of Brucella broth, but were not further treated with any experimental compounds. H. bilis infections were done at the beginning of the study (day 0) and repeated one week later (day 7).

Treatment

Treatment groups were assigned by cage, not by randomization of individual mice; thus all mice in a given cage received the same treatment. The groups were closely matched in weight on day 0 of the study. Mice were treated PO daily with the calcimimetic compound, R-Compound B, at doses of 10 mg/kg or 3 mg/kg. For controls, 100 µL of vehicle or 10 mg/kg of the less active enantiomer of Compound B, S-Compound B, were used. All treatments were given in 100 µL of vehicle beginning on day 1. As a positive control, mice were treated IP once per week with 250 µg of CTLA4-Fc in 100 µL of PBS beginning on day 1. All experimental compounds were generated at Amgen.

Treatment Group Design

TABLE 7

| Group No. | Treatment | No. of Mice | Day 0 Mean Weight ± SEM (g) | Route | Dose Level (mg/kg)[b] | Conc. (mg/mL) | Volume (mL) | Dosing Schedule[d] |
|---|---|---|---|---|---|---|---|---|
| 1 | Naive[a] | 5 | 21.04 ± 0.31 | NA[c] | NA | NA | 0.1 | NA |
| 2 | CTLA4-Fc | 5 | 19.92 ± 1.21 | IP | 0.0125 | 2.5 | 0.1 | 1x/week |
| 3 | Vehicle | 10 | 21.88 ± 0.41 | PO | NA | NA | 0.1 | 7x/week |
| 4 | S-Comp B | 5 | 20.16 ± 0.52 | PO | 10 | 2 | 0.1 | 7x/week |

TABLE 7-continued

| Group No. | Treatment | No. of Mice | Day 0 Mean Weight ± SEM (g) | Route | Dose Level (mg/kg)[b] | Conc. (mg/mL) | Volume (mL) | Dosing Schedule[d] |
|---|---|---|---|---|---|---|---|---|
| 5 | R-Comp B | 10 | 21.20 ± 0.49 | PO | 10 | 2 | 0.1 | 7x/week |
| 6 | R-Comp B | 10 | 21.01 ± 0.26 | PO | 3 | 0.6 | 0.1 | 7x/week |

[a]Naïve animals were control infected with Brucella broth, but received no experimental treatment
[b]Based on a 20 g mouse
[c]Not applicable
[d]Dosing began on day 1

Assessment of Colitis

Mice were monitored at least 3 times per week for clinical signs of colitis. Clinical scoring criteria consisted of two parts: fecal consistency and anal inflammation. Fecal consistency was scored as follows: 0=Normal stool, 1=Dirty anus, 2=Soft or moist stool, 3=Diarrhea, 4=Bloody stool. Anal inflammation was scored as follows: 0=No inflammation, 1=Mild inflammation, 2=Moderate inflammation, 3=Severe inflammation, 4=Prolapsed rectum. The individual scores for each mouse were summed, and the total was reported as the clinical score (maximum of 8).

Necropsy Procedures

All mice were necropsied on day 38 post initial inoculation. Mice were euthanized by $CO_2$ asphyxiation. Blood was obtained by intracardiac puncture and collected in serum separator tubes. Serum was harvested and stored at −80° C. Colons were dissected below the cecum and just above the anus, and the contents of the lumen were removed. Sections of the proximal, middle, and distal colon regions were fixed in 10% neutral buffered formalin for histopathological analysis.

Serum Analysis: Clinical Chemistry and Chemokines

Serum clinical chemistry analysis was performed on the Olympus AU400 using standard tests and protocols. Calcium and phosphorus measurements were performed on undiluted serum for all samples. Serum cytokines and chemokines were assayed by Lincoplex mouse cytokine/chemokine muliplex immunoassay (Millipore; Billerica, Mass.) per manufacturer instructions.

Histology

Portions from the proximal, middle, and distal colon were placed into 10% neutral buffered formalin, processed, and paraffin embedded using routine histology practices. Hematoxylin and eosin stained slides were prepared using routine histology protocols. One 5 μm section per colon sample was evaluated and scored using the criteria of Maggio-Price et al. from 2002 (supra): 0=no inflammation; 1=mild inflammation limited to mucosa; 2=moderate inflammation in mucosa and submucosa; 3=severe inflammation with obliteration of normal architecture, superficial erosions and/or crypt abscesses; 4=severe inflammation with obliteration of normal architecture, superficial erosions and/or crypt abscesses plus mucosal ulceration. For each animal, the histology score is the total of individual section scores.

Statistical Analysis

Results for serum analytes were expressed as the mean±standard error of the mean (SEM). A one-way ANOVA with Tukey's post test was performed using GraphPad Prism. A p-value of 0.05 was used in the calculation to determine whether there were significant differences between any two groups. Results for disease onset were expressed as a standard survival curve. A Log-Rank (Mantel-Cox) Test was performed using GraphPad Prism to determine significance. A p-value of 0.05 was used in the calculation to determine whether there were significant differences between any two groups. Results for clinical score and histology score were expressed as the mean±SEM. A Cochran-Mantel-Haenszel mean score test was performed using SAS software. A p-value of 0.05 was used in the calculation to determine whether there were significant differences between any two groups.

EXAMPLE 2

This experiment demonstrates the effect of calcimimetics on inflammation in the DSS-induced mice model of IBD.

For disease induction, treated mice were given 5% DSS in water ad libitum as drinking water for 9 days as described in Example 1 and were concurrently treated orally during that period with one of the treatments listed in Table 8.

TABLE 8

| 5% DSS | Treatment | Dose | Route |
|---|---|---|---|
| no | Untreated (normal) | n/a | n/a |
| yes | Calcimimetic Compound B | 10 mg/kg | oral |
| yes | FK 506 | 1 mg/kg | oral |
| yes | Captisol (vehicle) | 200 μl | oral |

FIG. 1 and Table 8 summarize the effect of the calcimimetic compound B on colonic inflammation in 5% DSS induced colitis. Animals were euthanized with carbon dioxide on day nine post treatment. The large intestine (colon) was removed and processed for histopathologic changes of the proximal, middle and distal segments as described in Example 1. The intestine was scored as a global assessment of inflammation based on inflammatory infiltrate, edema, mucosal erosions or ulcerations as indicated in Table 6. All samples were scored in a blinded fashion.

Treatment of SJL/J female mice with 5% DSS ad libitum in their drinking water for 9 days induced detectable histomorphologic inflammatory changes in all segments of the large intestine (FIG. 1, panels A, B, and C, vehicle treated animals). Treatment with 10 mg/kg of Compound B resulted in statistically significant decreased mean large intestine inflammatory scores in distal ($p<0.05$, FIG. 1C), middle ($p<0.01$, FIG. 1B) and combined segments ($p<0.01$, FIG. 1D) when compared to the Captisol vehicle group. Four out of ten calcimimetic-treated animals lacked inflammatory changes, indicating that their colon was normal (Table 9). Additionally, treatment with Compound B resulted in statistically significant ($p<0.05$) decrease in mean inflammatory score in combined colonic segments when compared to FK 506 treatment (positive control, Table 9).

TABLE 9

| 5% DSS | Treatment | Dose | Animals with colonic inflammation/total animals |
|---|---|---|---|
| no | Untreated (normal) | n/a | 0/10 |
| yes | Compound B | 10 mg/kg | 6/10 |
| yes | FK 506 | 1 mg/kg | 10/10 |
| yes | Captisol (vehicle) | 200 µl | 10/10 |

In a separate study calcimimetic compounds that have been demonstrated not to be absorbed readily from the gut into the bloodstream (Compounds C and D) were evaluated on mouse colonic inflammation in 5% DSS induced colitis. Animals were euthanized with carbon dioxide on day nine post treatment. The large intestine (colon) was removed and processed for histopathologic changes of the proximal, middle and distal segments as described in Example 1. The intestine was scored as a global assessment of inflammation based on inflammatory infiltrate, edema, mucosal erosions or ulcerations as indicated in Table 6. All samples were scored in a blinded fashion.

TABLE 10

| 5% DSS | Treatment | Dose | Route |
|---|---|---|---|
| no | Untreated (normal) | n/a | n/a |
| yes | Compound C | 30 mg/kg | oral |
| yes | Compound D | 30 mg/kg | oral |
| yes | Captisol (vehicle) | 200 µl | oral |

Figure 2A:
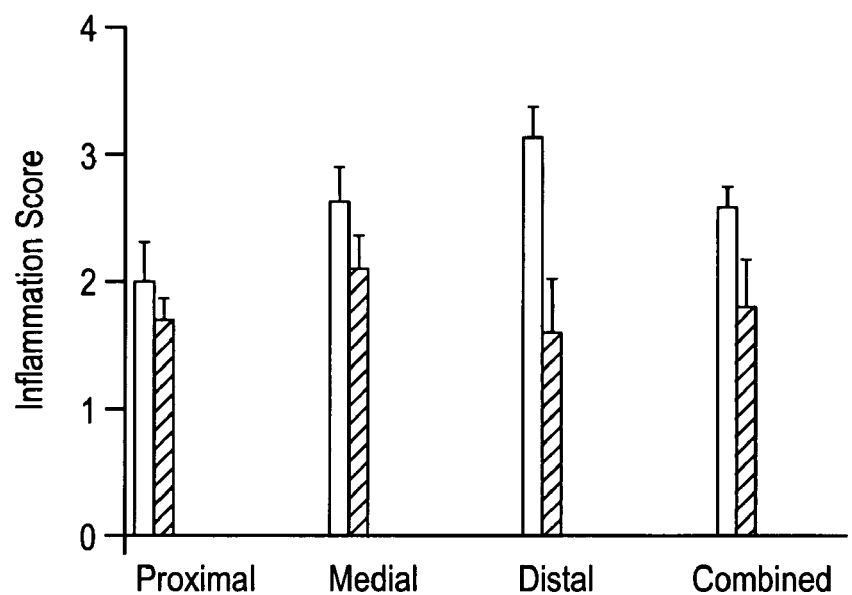
FIG. 2 demonstrates that the calcimimetics Compound C (Panel A) and Compound D (Panel B) reduce inflammation scores in all parts of colon compare to the vehicle. Open bars, vehicle; black bars, calcimimetics.

Treatment of SJL/J female mice with 5% DSS ad libitum in their drinking water for 9 days induced detectable histomorphologic inflammatory changes in all segments of the large intestine (FIG. 2A, Captisol vehicle treated animals—open bars). Treatment with 30 mg/kg of Compound C resulted in decreases in mean large intestine inflammatory scores in distal (49%, p<0.05), middle (20%), proximal (15%) and combined (30%) colon segments (FIG. 2A, black bars) when compared to the Captisol vehicle group (open bars).

Figure 2B:
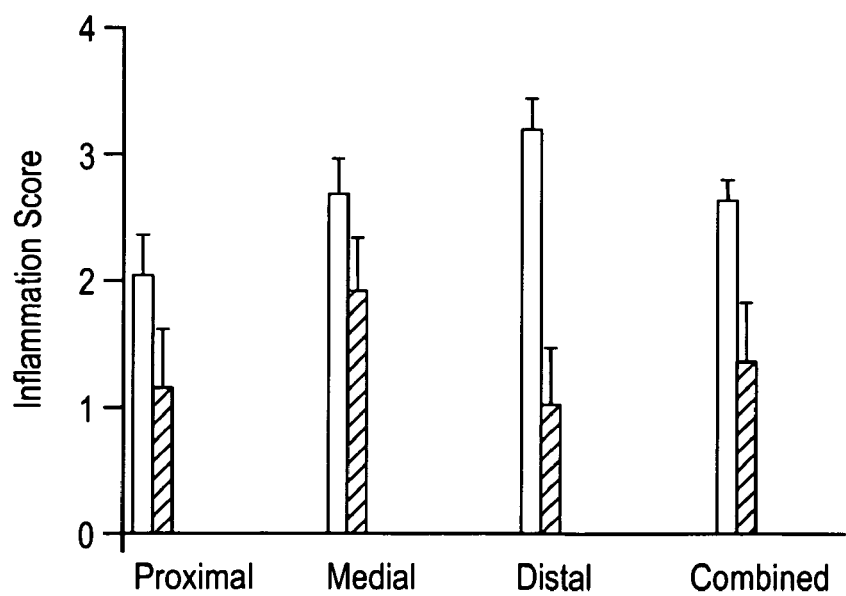
Figure 3A:
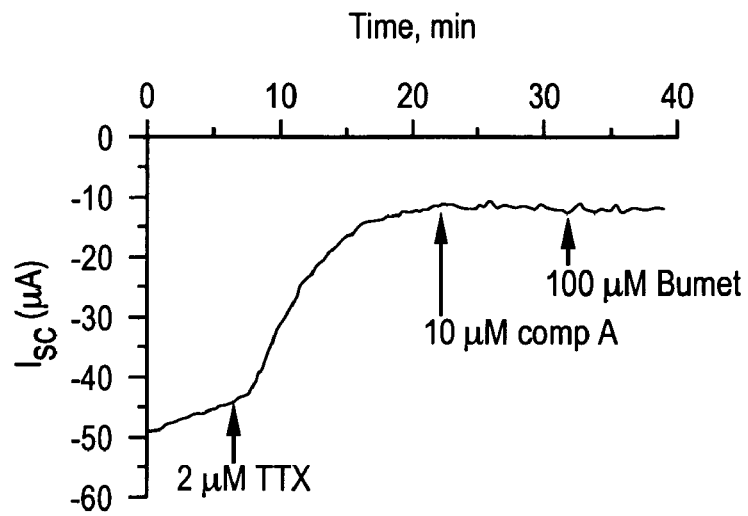
FIG. 3 illustrates the changes in short-circuit secretory current in the absence and presence of 2 µM TTX, before and after addition of 10 µM of a calcimimetic Compound A, before and after the addition of 100 µM bumetanide, an inhibitor of chloride secretion.
Figure 3B:
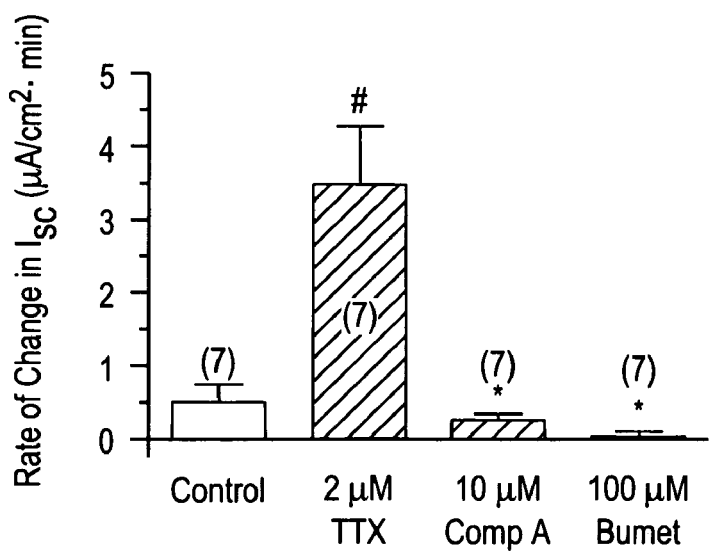
Figure 3C:
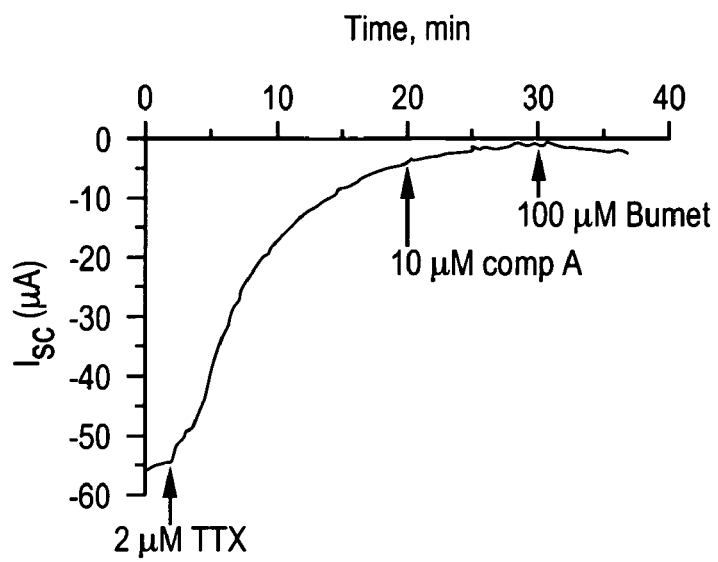
Figure 3D:
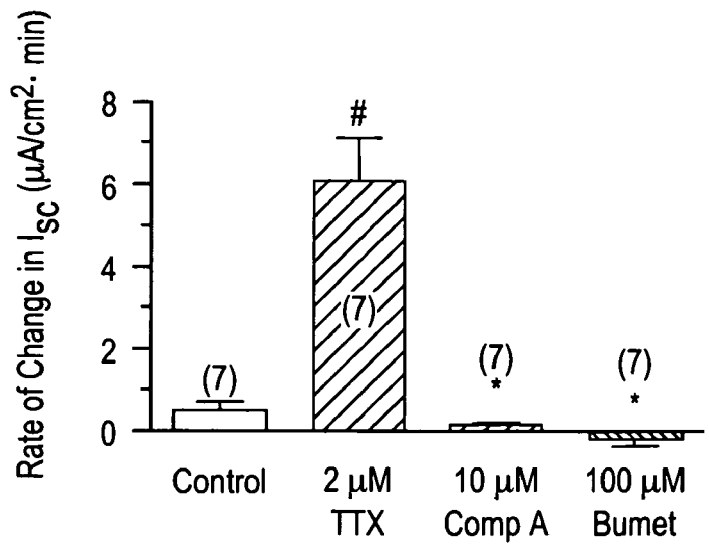
Figure 4A:
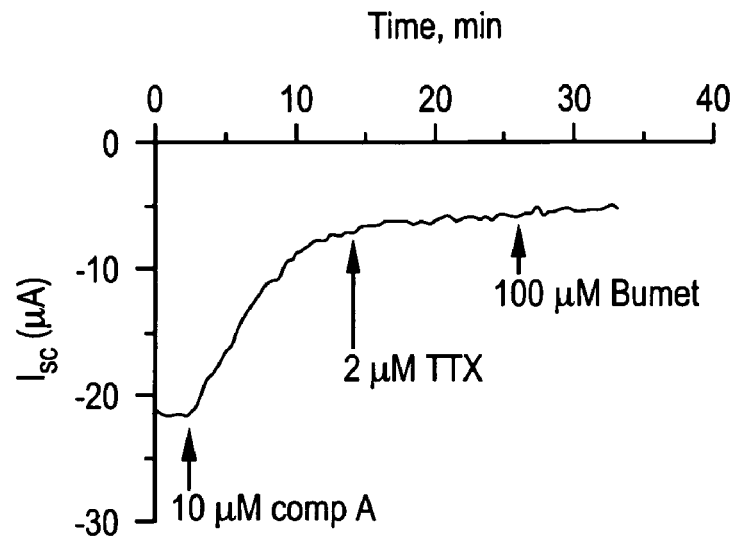
FIG. 4 illustrates the changes in short-circuit secretory current in the absence and presence of 10 µM of Compound A, before and after addition of 2 µM TTX, before and after the addition of 100 µM bumetanide.
Figure 4B:
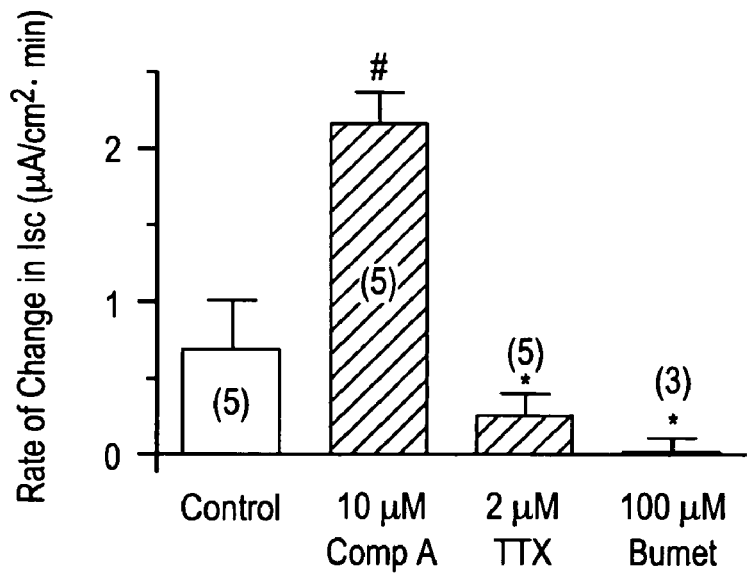
Figure 4C:
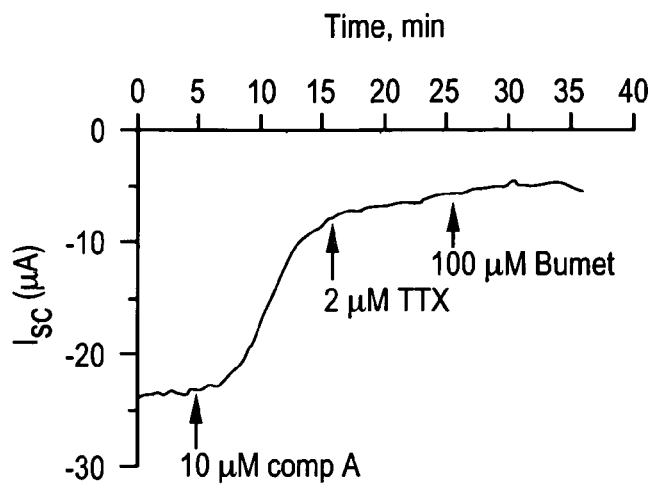
Figure 4D:
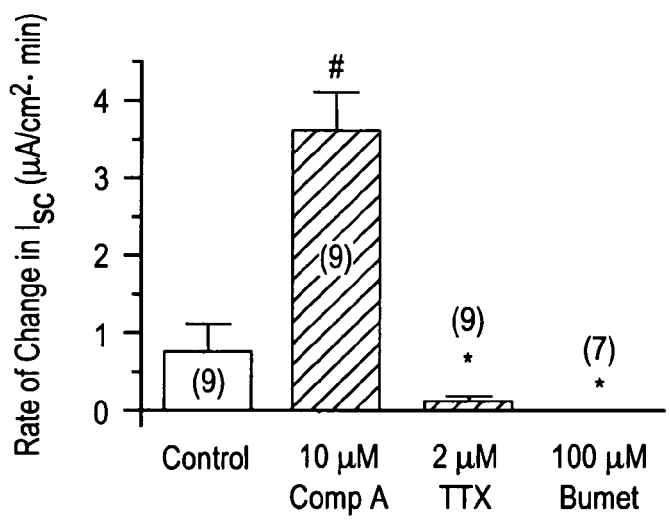

Treatment with 30 mg/kg of Compound D resulted in decreases in mean large intestine inflammatory scores in distal (68%; p<0.01), middle (29%), proximal (44%; p<0.05) and combined (48%; p<0.05) segments when compared to the Captisol vehicle group (FIG. 2B, Captisol vehicle-treated animal, open bars; calcimimetic Compound D-treated animals, black bars). Two out of eight Compound D treated animals lacked inflammatory changes, indicating that their colon was normal.

EXAMPLE 3

This example demonstrates that calcimimetics inhibit enteric nervous system activity. To assess the functional relevance of the CaSR in the Enteric Nervous System (ENS), particularly in its ability to inhibit the secretory response to secretagogues released from ENS activity, the effect of CaSR activation on basal short-circuit secretory current was determined in rat unstripped colonic sheets mounted in Ussing chambers before or after blocking ENS nervous activity by the voltage-activated sodium channel inhibitor, tetrodotoxin, TTX.

FIG. 3 summarizes the changes in short-circuit secretory current in the absence and presence of 2 µM TTX, before and after addition of 10 µM of a calcimimetic Compound A, before and after the addition of 100 µM bumetanide, an inhibitor of chloride secretion. Representative traces of the temporal changes in short-circuit current are shown for Proximal (Panel A) and Distal (Panel C) colon before and after addition of the agents indicated by arrows. TTX inhibited the secretory short-circuit current over 15 minutes. Subsequent addition of Compound A or bumetanide (Bumet) had no additional effect on short-circuit current. The rates of change in short-circuit current ($\mu A/cm^2$ min) induced by addition of these agents are summarized for Proximal (Panel B) and Distal (Panel D) colon sheets. The number in parentheses indicates the number of observations.

FIG. 4 summarizes the changes in short-circuit secretory current in the absence and presence of 10 µM of Compound A, a calcimimetic, before and after addition of 2 µM TTX, an inhibitor of ENS activity, before and after the addition of 100 µM bumetanide, an inhibitor of chloride secretion. Representative traces of the temporal changes in short-circuit current are shown for Proximal (A) and Distal (C) colon before and after addition of the agents indicated by arrows. Compound A inhibited the secretory short-circuit current over 15 minutes. Subsequent addition of TTX or bumetanide (Bumet) had no additional effect on short-circuit current. The rates of change in short-circuit current ($\mu A/cm^2$ min) induced by addition of these agents are summarized for Proximal (B) and Distal (D) colon sheets. The number in parentheses indicates the number of observations.

EXAMPLE 4

This example demonstrates that the calcimimetic R-Compound B attenuates the development of colitis in mdr1a$^{-/-}$ mice.

On the final day of the study, 50% of the mice in the vehicle control group showed clinical symptoms of disease and all of those animals had clinical scores ≧6 (FIG. 5). Only one animal in the S-Compound B treated group had clinical symptoms, and it had a score of 4, suggesting moderate disease. In each of the R-Compound B treatment groups, only one animal showed clinical signs of disease on the final day of the study. Of the R-Compound B treated animals that did show clinical symptoms, none had an anal inflammation score above moderate, and no animal developed diarrhea. Of note, the R-Compound B 10 mg/kg group had significantly lower clinical scores than the vehicle group (p<0.05). The uninfected and CTLA4-Fc treated animals showed no clinical symptoms throughout the study.

Disease onset began on day 14 in the vehicle treated group, and by the end of the study, half of the vehicle treated mice were sick (FIG. 6). The S-Compound B group began showing symptoms on day 27, at which point two animals had clinical signs of disease. Disease persisted until the end of the study in only one of these animals. One animal treated with 3 mg/kg of R-Compound B began showing clinical signs of colitis on day 17. A second animal developed signs of disease on day 31, but this did not persist through the end of the study. One animal from the 10 mg/kg group began showing clinical symptoms on day 32, and this was the only mouse in this group to appear colitic. There was a statistically significant difference in disease onset between the vehicle control group and the R-Compound B 10 mg/kg group (p-value=0.04). Taken together, these data strongly suggest that treatment with R-Compound B delayed the onset of colitis and reduced the severity of disease.

Post Mortem Analysis

Histological examination demonstrated that 10 animals in the study had evidence of colitis (Table 11).

TABLE 11

S08M-00850 Histopathology Results

Group 1 Uninfected/untreated

| Microscopic Findings | Animal Nos. | | | | | Segment |
|---|---|---|---|---|---|---|
| GI Inflammation | 1 | 2 | 3 | 4 | 5 | Mean |
| LI PROXIMAL | 0 | 0 | 0 | 0 | 0 | 0.00 |
| LI MIDDLE | 0 | 0 | 0 | 0 | 0 | 0.00 |
| LI DISTAL | 0 | 0 | 0 | 0 | 0 | 0.00 |
| Total LI score (Max = 12) | 0 | 0 | 0 | 0 | 0 | |
| Average LI score | 0 | | | | | |

Group 2 250 μg CTLA4-Fc

| Microscopic Findings | Animal Nos. | | | | | | | | | | Segment |
|---|---|---|---|---|---|---|---|---|---|---|---|
| GI Inflammation | 1 | 2 | 3 | 4 | 5 | 6 | 7 | 8 | 9 | 10 | Mean |
| LI PROXIMAL | 0 | 0 | 0 | 0 | 0 | | | | | | 0.00 |
| LI MIDDLE | 0 | 0 | 0 | 0 | 0 | | | | | | 0.00 |
| LI DISTAL | 0 | 0 | 0 | 0 | 0 | | | | | | 0.00 |
| Total LI score (Max = 12) | 0 | 0 | 0 | 0 | 0 | | | | | | |
| Average LI score | 0 | | | | | | | | | | |

Group 3 100 μl Vehicle Alone

| Microscopic Findings | Animal Nos. | | | | | | | | | | Segment |
|---|---|---|---|---|---|---|---|---|---|---|---|
| GI Inflammation | 1 | 2 | 3 | 4 | 5 | 6 | 7 | 8 | 9 | 10 | Mean |
| LI PROXIMAL | 0 | 3 | 0 | 3 | tnp | 0 | 0 | 3 | 3 | 3 | 1.67 |
| LI MIDDLE | 0 | 4 | 0 | 3 | tnp | 0 | 0 | 3 | 3 | 3 | 1.78 |
| LI DISTAL | 0 | 3 | 0 | 3 | tnp | 0 | 0 | 3 | 3 | 3 | 1.67 |
| Total LI score (Max = 12) | 0 | 10 | 0 | 9 | | 0 | 0 | 9 | 9 | 9 | |
| Average LI score | 5.1 | | | | | | | | | | |

Group 4 10 mg/kg S-B PO Daily

| Microscopic Findings | Animal Nos. | | | | | | | | | | Segment |
|---|---|---|---|---|---|---|---|---|---|---|---|
| GI Inflammation | 1 | 2 | 3 | 4 | 5 | 6 | 7 | 8 | 9 | 10 | Mean |
| LI PROXIMAL | 0 | 3 | 0 | 0 | 0 | | | | | | 0.60 |
| LI MIDDLE | 0 | 3 | 0 | 0 | 0 | | | | | | 0.60 |
| LI DISTAL | 0 | 3 | 0 | 0 | 0 | | | | | | 0.60 |
| Total LI score (Max = 12) | 0 | 9 | 0 | 0 | 0 | | | | | | |
| Average LI score | 1.8 | | | | | | | | | | |

Group 5 10 mg/kg R-B PO Daily

| Microscopic Findings | Animal Nos. | | | | | | | | | | Segment |
|---|---|---|---|---|---|---|---|---|---|---|---|
| GI Inflammation | 1 | 2 | 3 | 4 | 5 | 6 | 7 | 8 | 9 | 10 | Mean |
| LI PROXIMAL | 2 | 0 | 0 | 0 | 2 | 0 | 0 | 0 | 0 | 0 | 0.40 |
| LI MIDDLE | 0 | 0 | 0 | 0 | 2 | 0 | 0 | 0 | 0 | 0 | 0.20 |
| LI DISTAL | 0 | 0 | 0 | 0 | 3 | 0 | 0 | 0 | 0 | 0 | 0.30 |
| Total LI score (Max = 12) | 2 | 0 | 0 | 0 | 7 | 0 | 0 | 0 | 0 | 0 | |
| Average LI score | 0.9 | | | | | | | | | | |

Group 6 3 mg/kg R-B PO Daily

| Microscopic Findings | Animal Nos. | | | | | | | | | | Segment |
|---|---|---|---|---|---|---|---|---|---|---|---|
| GI Inflammation | 1 | 2 | 3 | 4 | 5 | 6 | 7 | 8 | 9 | 10 | Mean |
| LI PROXIMAL | 0 | 0 | 0 | 0 | 2 | 0 | 0 | 0 | 2 | 0 | 0.40 |
| LI MIDDLE | 0 | 0 | 0 | 0 | 3 | 0 | 0 | 0 | 3 | 0 | 0.60 |
| LI DISTAL | 0 | 0 | 0 | 0 | 3 | 0 | 0 | 0 | 3 | 0 | 0.60 |
| Total LI score (Max = 12) | 0 | 0 | 0 | 0 | 8 | 0 | 0 | 0 | 8 | 0 | |
| Average LI score | 1.6 | | | | | | | | | | |

Scoring criteria are described Example 1. Scores from each section of the colon were summed to generate a total large intestine (LI) score. The maximum LI score for each mouse was 12. Mouse 3-5 was found dead in its cage, so the tissue was not present (tnp).

Figure 7:
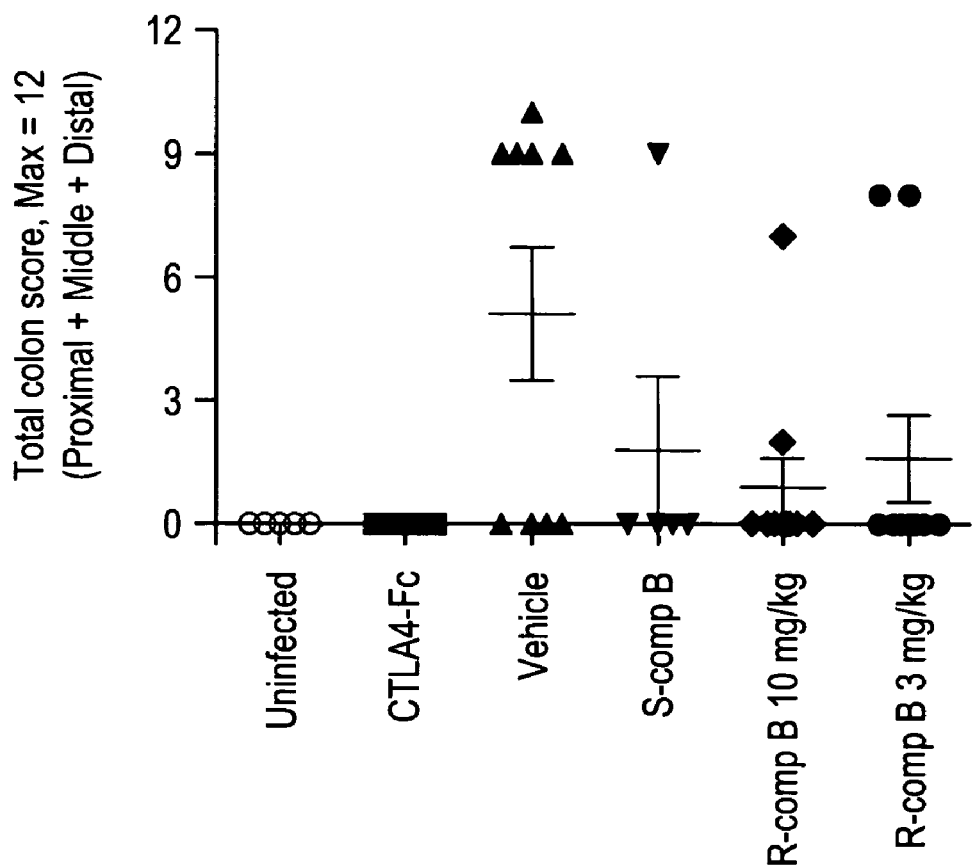
FIG. 7 illustrates histology score. Histology scores represent the sums of scores given to the three section of colon taken: proximal, middle, and distal. The scoring system for each section is described in the methods. Error bars represent SEM.

In the vehicle treated group, 5 out of 9 animals (55%) had colitis, while 2 out of 10 animals (20%) in each of the R-Compound B treated groups had colon pathology (FIG. 7). The total large intestine (LI) scores of the colitic mice in the vehicle group were all $\geq 9$, while scores of the R-Compound B treated animals were 8, 8, 7, and 2. Taken together, these data indicate that treatment with R-Compound B reduced the incidence and severity of disease. In the S-Compound B group, 1 out of 5 animals developed colitis. This single afflicted animal had a colon pathology score of 9, indicating severe disease. Uninfected and CTLA4 treated mice showed no signs of disease.

Figure 8A:
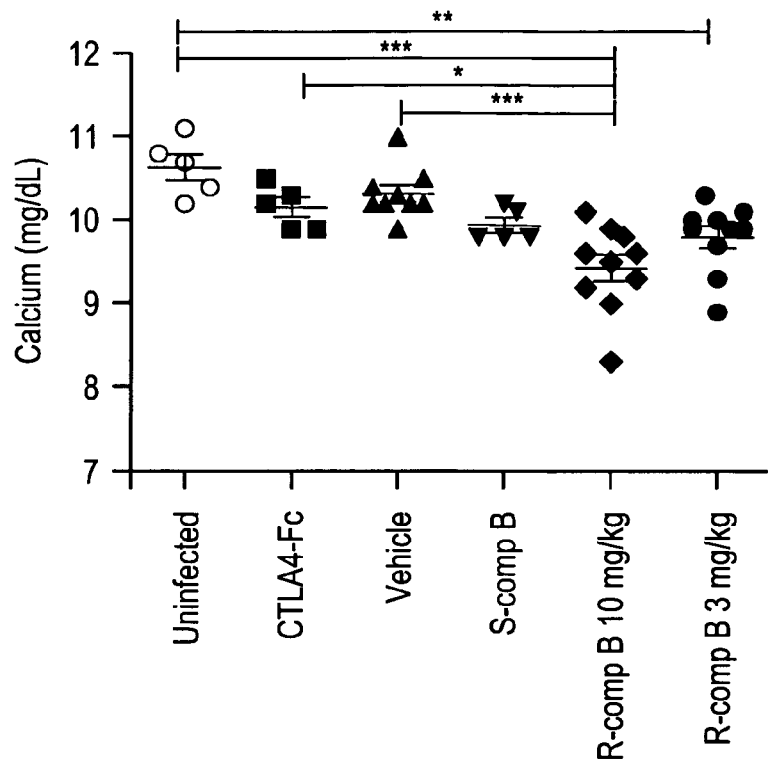
FIG. 8 demonstrates the effect of calcimimetics on serum calcium (panel A) and phosphorus (panel B). Error bars represent SEM.
Figure 8B:
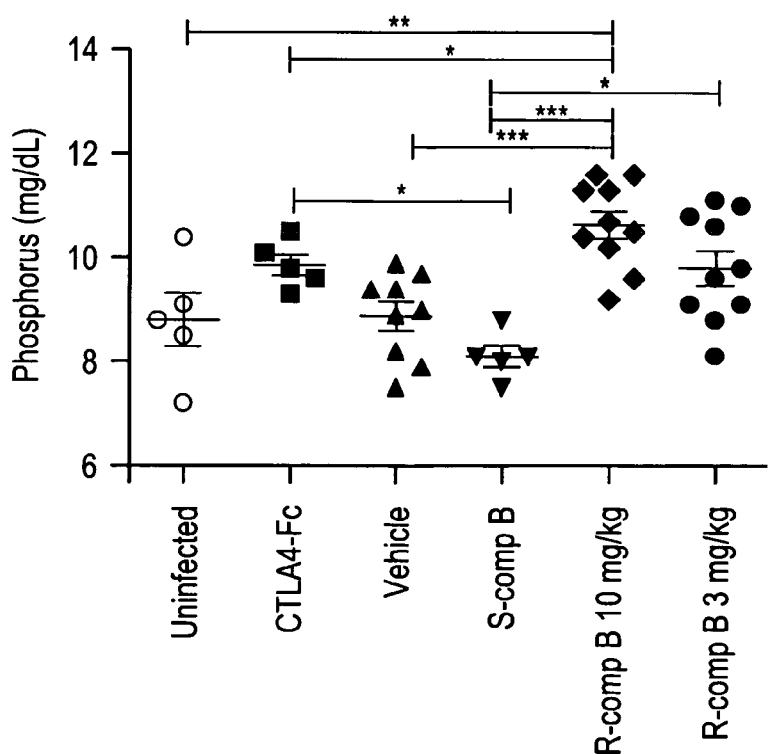

Serum calcium levels were significantly reduced in both R-Compound B treatment groups compared to the uninfected controls (FIG. 8). R-Compound B at the 10 mg/kg dose also induced significant calcium reductions compared to the CTLA4 and vehicle control groups. Calcium levels in the S-Compound B group were not statistically different from any other group. Serum phosphorus levels were significantly elevated in the R-Compound B 10 mg/kg group compared to all control groups. The lower 3 mg/kg dose induced a significant elevation in serum phosphorus compared to the S-Compound B treated group only. S-Compound B induced a significant reduction in phosphorus compared to CTLA4 treated animals. In all, these data demonstrate that the calcimimetic compound was biologically active, and that the higher dose generated more pronounced effects.

Figure 9:
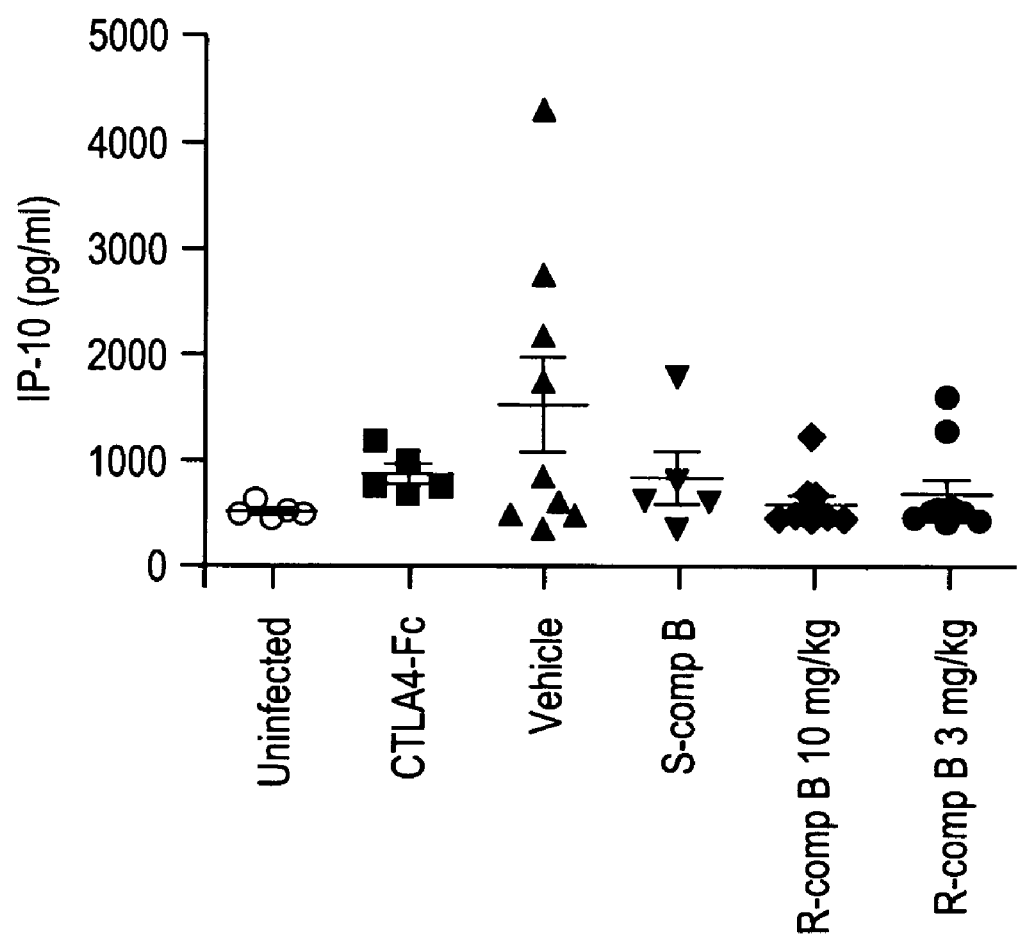
FIG. 9 demonstrates the effect of calcimimetics on serum IP-10 levels. Error bars represent SEM.

Finally, to provide further evidence in the serum that calcimimetic treatment helped to prevent colitis, a panel of cytokines and chemokines was measured. Of these, IP-10, a chemokine that can play a role in cell migration, was the most clearly impacted by R-Compound B treatment (FIG. 9). The difference in production of IP-10 between the R-Compound B 10 mg/kg group and the vehicle control group approached significance (p=0.06), but overall there was no statistically significant difference between any of the groups. Serum IP-10 levels were elevated in vehicle treated animals that demonstrated clinical symptoms of disease, and they correlated with the severity of the disease as measured by clinical score. This correlation with severity was present in every treatment group. In the R-Compound B and S-Compound B groups, less elevation of IP-10 was observed, further suggesting a protective benefit.

Overall, treatment with R-Compound B inhibited the development and severity of colitis in mdr1a$^{-/-}$ mice. This was confirmed both by clinical and histopathological scoring, and by reduction of the inflammatory chemokine IP-10. Overall, there is a definite, statistically significant trend in some of the measurements used to track the development of colitis that suggest that treatment with calcimimetic compounds, such as R-Compound B, can attenuate the development of disease.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating an inflammatory bowel disease (IBD), comprising administering to a subject in need thereof a therapeutically effective amount of compound (1R)-N-((6-(methyloxy)-4'-(trifluoromethyl)-3-biphenylyl)methyl)-1-phenylethanamine, or a pharmaceutically acceptable salt thereof.

2. A method of treating an inflammatory bowel disease (IBD), comprising administering to a subject in need thereof a therapeutically effective amount of compound (1R)-N-((6-chloro-3'-fluoro-3-biphenylyl)methyl)-1-(3-chlorophenyl) ethanamine, or a pharmaceutically acceptable salt thereof.

3. A method of treating an inflammatory bowel disease (IBD), comprising administering to a subject in need thereof a therapeutically effective amount of compound (1R)-1-(6-(methyloxy)-4'-(trifluoromethyl)-3-biphenylyl)-N-((1R)-1-phenylethyl)ethanamine, or a pharmaceutically acceptable salt thereof.

* * * * *